US012604416B2

(12) United States Patent　　　(10) Patent No.:　US 12,604,416 B2
　　Obata et al.　　　　　　　　　　(45) Date of Patent:　Apr. 14, 2026

(54) LAMINATE FOR WIRING BOARD

(71) Applicant: NAMICS CORPORATION, Niigata (JP)

(72) Inventors: Naoki Obata, Niigata (JP); Makiko Sato, Niigata (JP)

(73) Assignee: NAMICS CORPORATION, Niigata (JP)

( * ) Notice: Subject to any disclaimer, the term of this patent is extended or adjusted under 35 U.S.C. 154(b) by 146 days.

(21) Appl. No.: 18/283,537

(22) PCT Filed: Jun. 10, 2021

(86) PCT No.: PCT/JP2021/022221
　　§ 371 (c)(1),
　　(2) Date: Sep. 22, 2023

(87) PCT Pub. No.: WO2022/201563
　　PCT Pub. Date: Sep. 29, 2022

(65) Prior Publication Data
　　US 2024/0179849 A1　　May 30, 2024

(30) Foreign Application Priority Data

Mar. 25, 2021　(JP) ................................. 2021-052398

(51) Int. Cl.
　H05K 1/05　　　　(2006.01)
　G01N 23/20058　　(2018.01)
　G01N 23/20091　　(2018.01)
　G01N 33/00　　　(2006.01)
　　　　(Continued)

(52) U.S. Cl.
　CPC ......... H05K 3/18 (2013.01); G01N 23/20058 (2013.01); G01N 23/20091 (2013.01); G01N 33/00 (2013.01); H05K 1/05 (2013.01); H05K 3/38 (2013.01); G01N 33/0096 (2024.05); H05K 2203/06 (2013.01)

(58) Field of Classification Search
　CPC ............... H05K 3/18; H05K 1/05; H05K 3/38
　See application file for complete search history.

(56) References Cited

U.S. PATENT DOCUMENTS

| 10,763,002 | B2 | 9/2020 | Matsuura | |
| 2004/0203235 | A1* | 10/2004 | Miyakawa | ............. C23C 18/08 257/E29.147 |

(Continued)

FOREIGN PATENT DOCUMENTS

| JP | 2002-176242 A | 6/2002 |
| JP | 2005-223226 A | 8/2005 |

(Continued)

OTHER PUBLICATIONS

International Search Report and Written Opinion for International Patent Application No. PCT/JP2021/022221, mailed Sep. 21, 2021, including partial English language translation (8 pages).

*Primary Examiner* — Jeremy C Norris

(74) *Attorney, Agent, or Firm* — Clark & Elbing LLP

(57) ABSTRACT

The present invention is directed to provide novel laminates for wiring boards. Novel laminates for wiring boards according to the present invention includes an insulating substrate layer and copper wiring, the laminate having a circuit linearity of 1.0 or more and 1.7 or less.

9 Claims, 27 Drawing Sheets

(A)

(A-1)

(1) PEER OFF THE COPPER FOIL LAID ON A CARRIER　(2) ELECTROLESS COPPER-PLATING　(3) RESIST LAMINATION　(4) ELECTROLYIC COPPER-PLATING　(5) PEER OFF THE RESIST　(6) REMOVAL OF THE SEED LAYER

ULTRA-THIN COPPER FOIL
RESIN
COPPER (A-2)

(1) TRANSFERRING OF FINE PROTRUSIONS　(2) ELECTROLESS COPPER-PLATING　(3) RESIST LAMINATION　(4) ELECTROLYIC COPPER-PLATING　(5) PEER OFF THE RESIST　(6) REMOVAL OF THE SEED LAYER

SEED LAYER

(51) Int. Cl.
    *H05K 3/18*      (2006.01)
    *H05K 3/38*      (2006.01)

(56)            References Cited

U.S. PATENT DOCUMENTS

| | | | | |
|---|---|---|---|---|
| 2009/0052214 | A1* | 2/2009 | Edo | H03K 17/18 |
| | | | | 363/123 |
| 2012/0181897 | A1* | 7/2012 | Masaki | H02N 1/08 |
| | | | | 310/309 |
| 2012/0247814 | A1 | 10/2012 | Shimizu et al. | |
| 2013/0001186 | A1* | 1/2013 | Sakaguchi | C23F 1/26 |
| | | | | 216/13 |
| 2013/0256006 | A1* | 10/2013 | Sakaguchi | H05K 1/09 |
| | | | | 174/254 |

FOREIGN PATENT DOCUMENTS

| | | | |
|---|---|---|---|
| JP | 2010-267891 | A | 11/2010 |
| JP | 2012-216773 | A | 11/2012 |
| JP | 2016-034010 | A | 3/2016 |
| JP | 2016-225524 | A | 12/2016 |
| JP | 2018-085465 | A | 5/2018 |
| KR | 10-2017-0116129 | A | 10/2017 |

* cited by examiner

(A)

(A-1)

(1) PEER OFF THE COPPER FOIL LAID ON A CARRIER

ULTRA-THIN COPPER FOIL
RESIN
COPPER (2) ELECTROLESS COPPER-PLATING (3) RESIST LAMINATION (4) ELECTROLYIC COPPER-PLATING (5) PEER OFF THE RESIST (6) REMOVAL OF THE SEED LAYER (A-2)

(1) TRANSFERRING OF FINE PROTRUSIONS

SEED LAYER (2) ELECTROLESS COPPER-PLATING (3) RESIST LAMINATION (4) ELECTROLYIC COPPER-PLATING (5) PEER OFF THE RESIST (6) REMOVAL OF THE SEED LAYER

FIG. 1A(A)

(B)
(B-1)
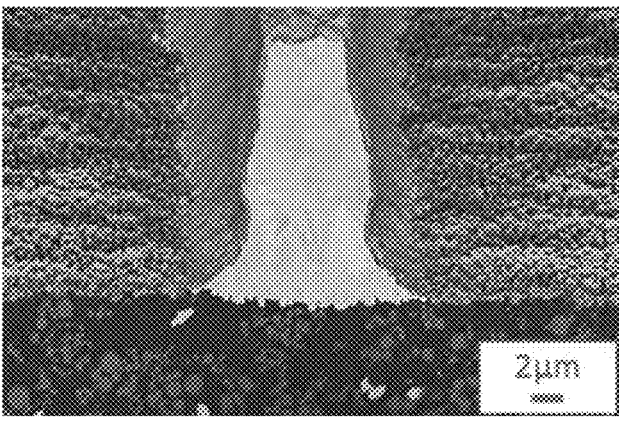
(B-2)
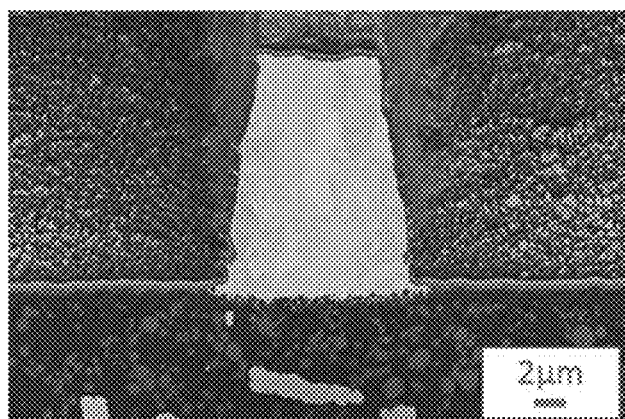
FIG. 1A(B)

(A)
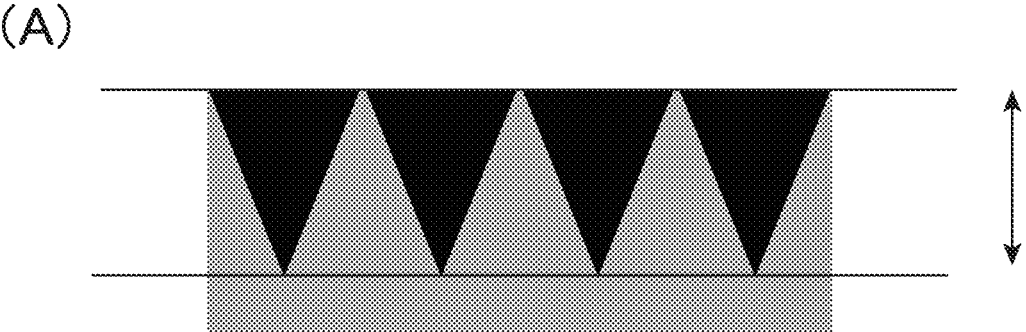
(B)
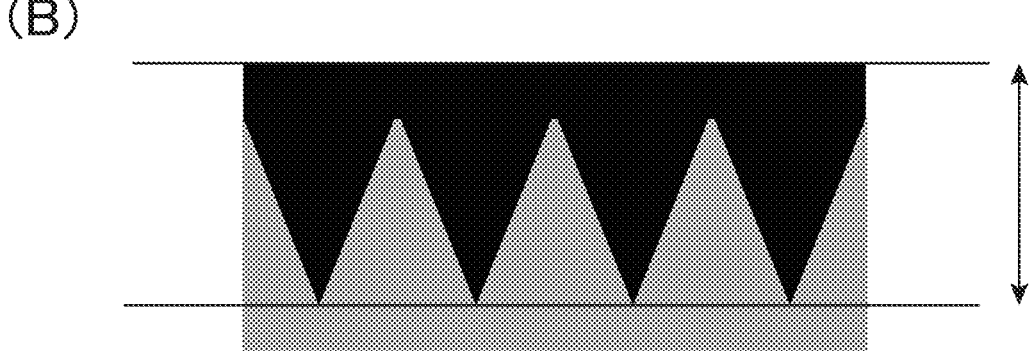
FIG. 1B

| | EXAMPLES | | | | | | | | COMPARATIVE EXAMPLES | | |
|---|---|---|---|---|---|---|---|---|---|---|---|
| | 1 | 2 | 3 | 4 | 5 | 6 | 7 | 8 | 2 | 3 | 4 |
| R5670KJ | O | O | O | O | O | O | O | O | × | × | × |
| R5680J | O | O | O | O | O | O | O | O | × | × | × |
| CT-Z | O | O | O | O | O | O | O | O | × | × | × |
| NX9255 | O | O | O | O | O | O | O | O | × | × | × |
| R1551GG | O | O | O | O | O | O | O | O | × | × | × |

FIG. 2-1 vsR5670KJ
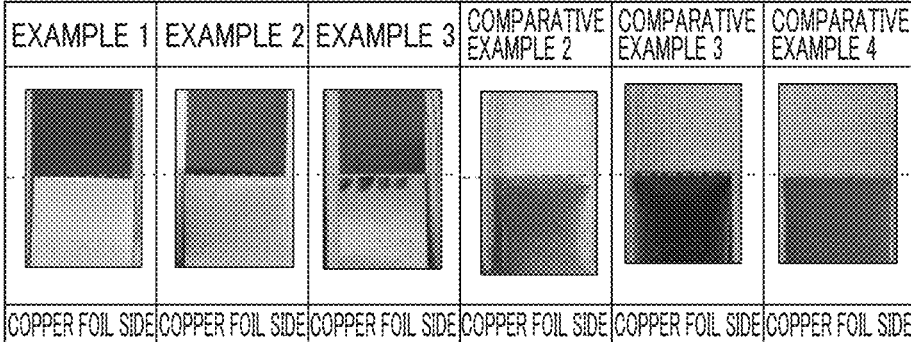
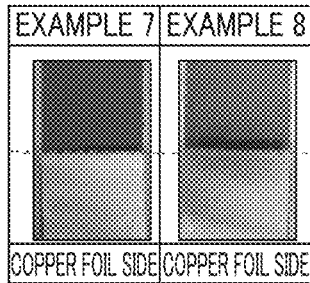
vsR5680KJ              vsCT−Z
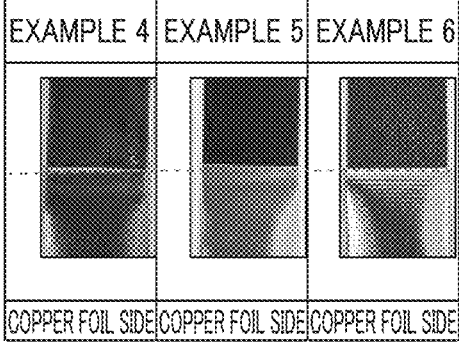 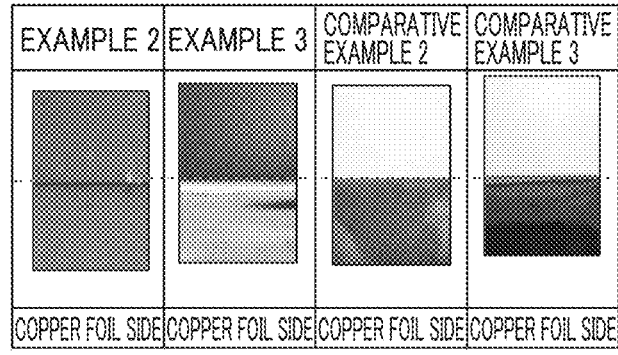
vsNX9255              vsR1551GG
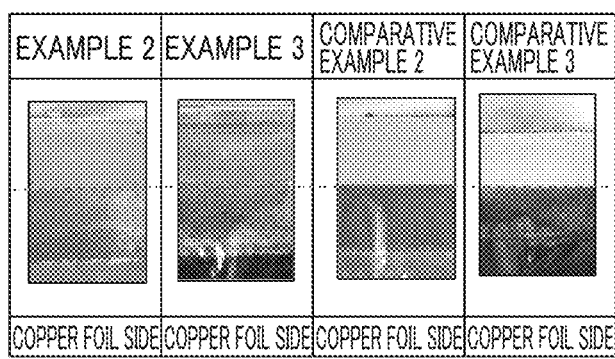 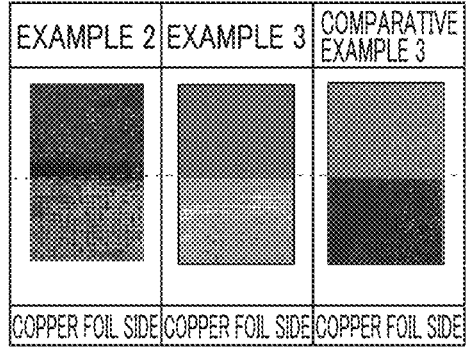
FIG. 2-2

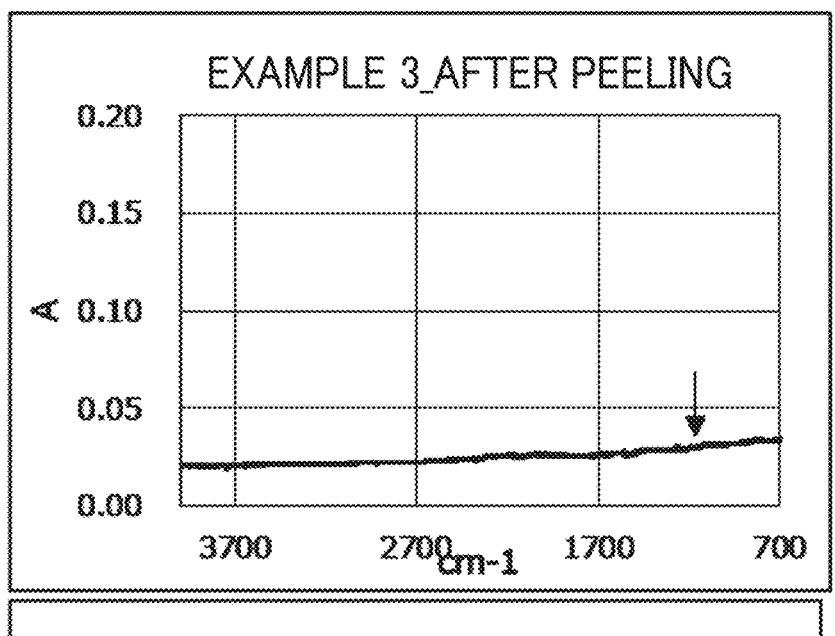
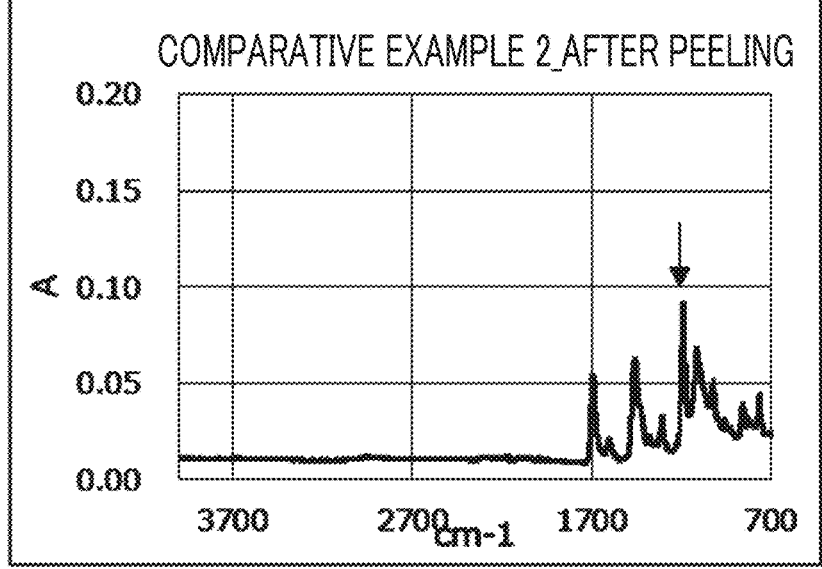
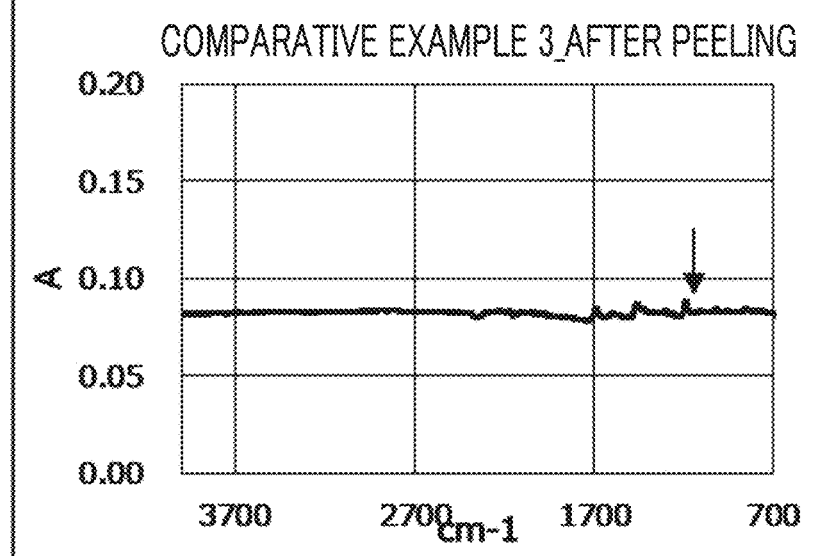
FIG. 4-2

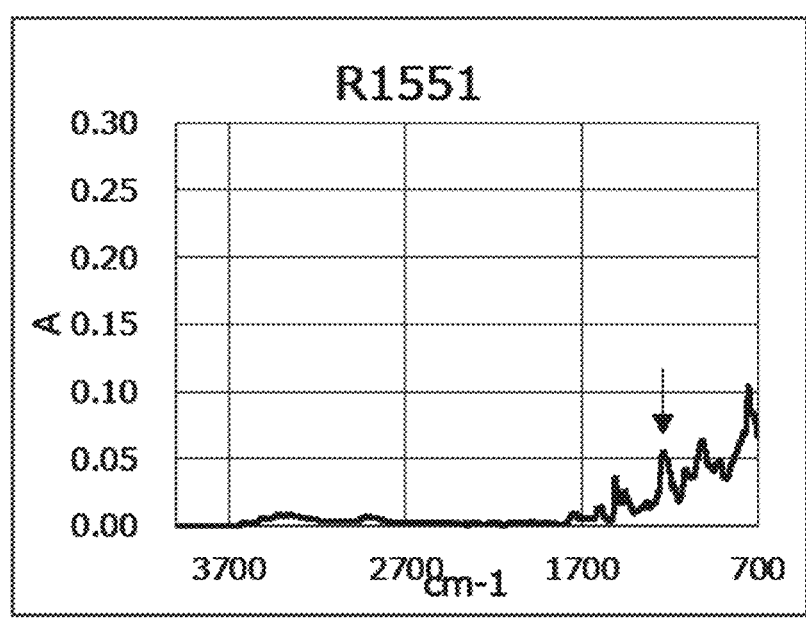
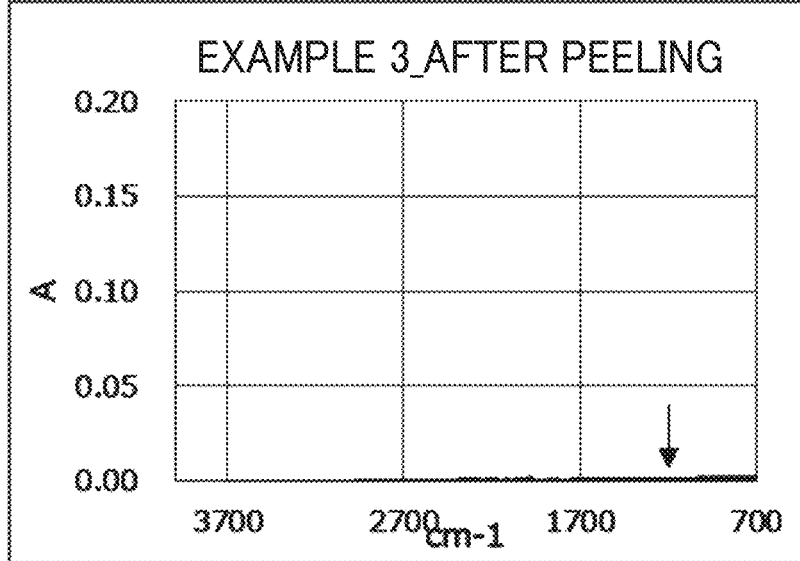
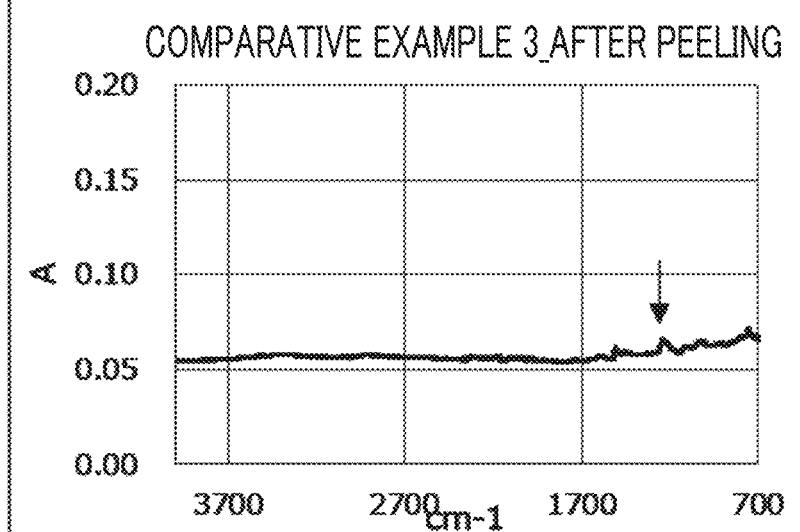
FIG. 5

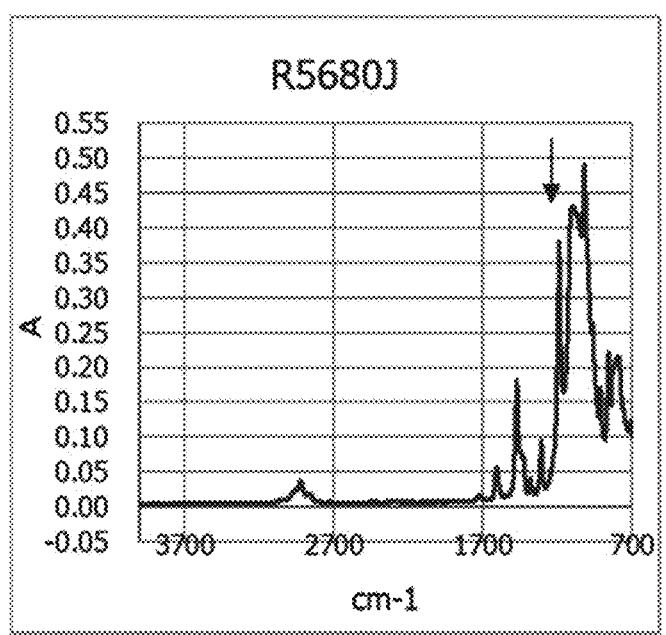
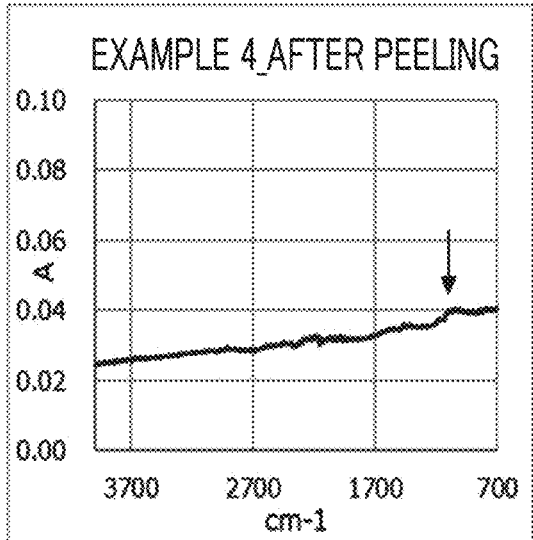
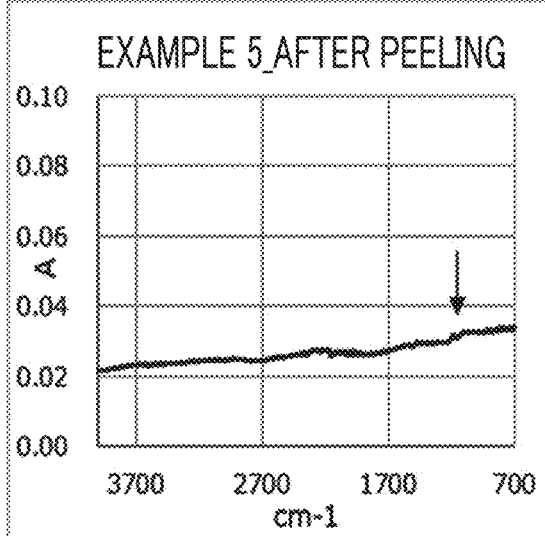
FIG. 6-1

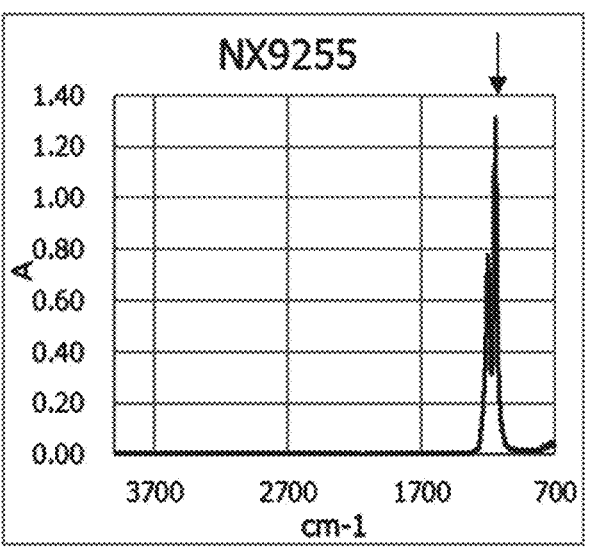
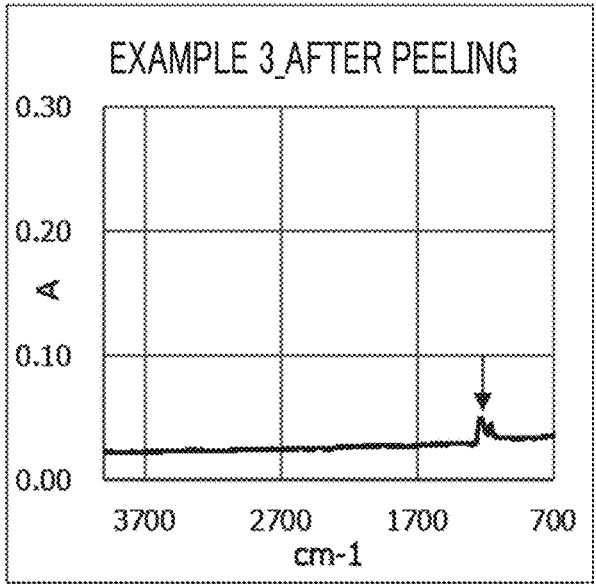
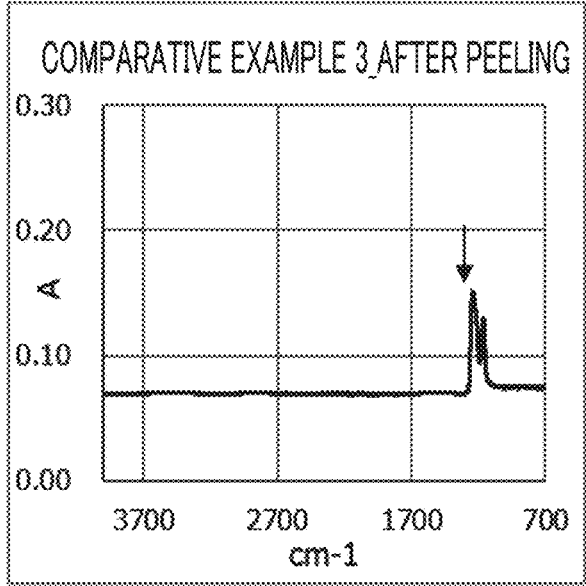
FIG. 7

FIG. 9A   EACH ELEMENT ALONE

| | SEM IMAGES (30000×) | MAPPING BY EDS | | | |
|---|---|---|---|---|---|
| | | C | O | Cu | Ni |
| EXAMPLE | RESIN / COPPER | | | | |
| COMPARATIVE EXAMPLE | RESIN / COPPER | | | | NO DETECTION |

FIG. 9B   OVERLAID

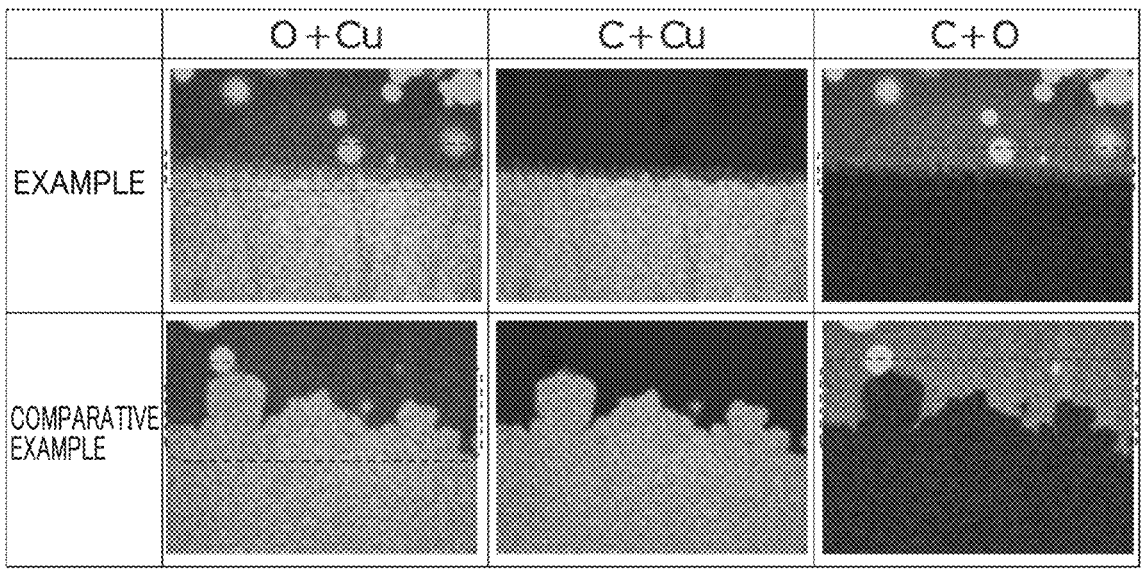

| | O+Cu | C+Cu | C+O |
|---|---|---|---|
| EXAMPLE | | | |
| COMPARATIVE EXAMPLE | | | |

FIG. 9C   SCHEMATIC DIAGRAM

▒ DETECTION PART    ▒ UNDETECTED PART      ▓ OVERLAPPING PART

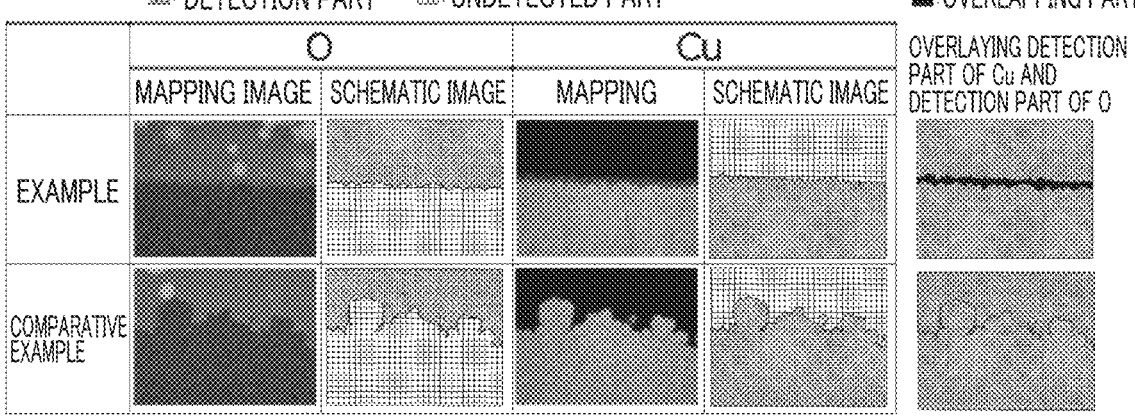

| | O | | Cu | | OVERLAYING DETECTION PART OF Cu AND DETECTION PART OF O |
|---|---|---|---|---|---|
| | MAPPING IMAGE | SCHEMATIC IMAGE | MAPPING | SCHEMATIC IMAGE | |
| EXAMPLE | | | | | |
| COMPARATIVE EXAMPLE | | | | | |

FIG. 11A    EXAMPLE
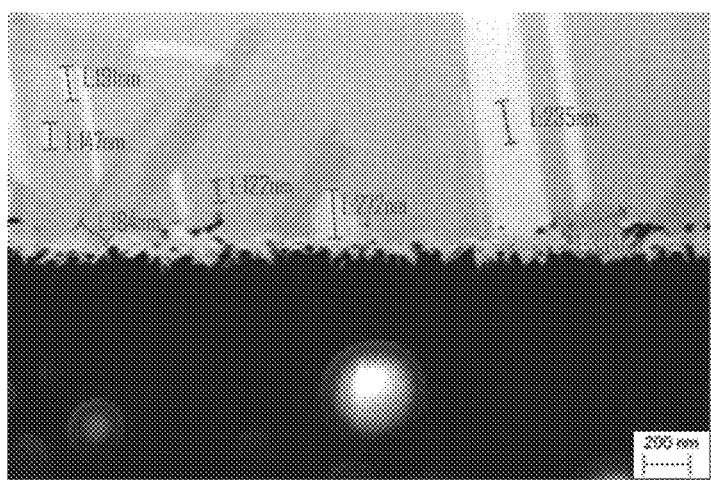
FIG. 11B    COMPARATIVE EXAMPLE: MAGNIFICATION 30,000 ×
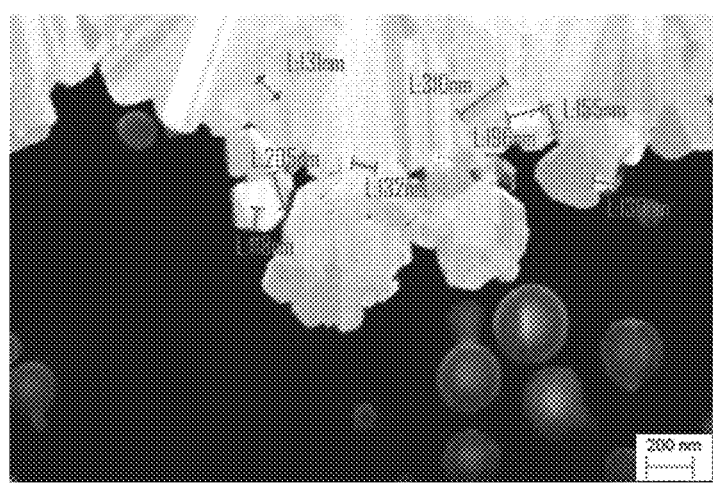
FIG. 11C    COMPARATIVE EXAMPLE: MAGNIFICATION 10,000 ×
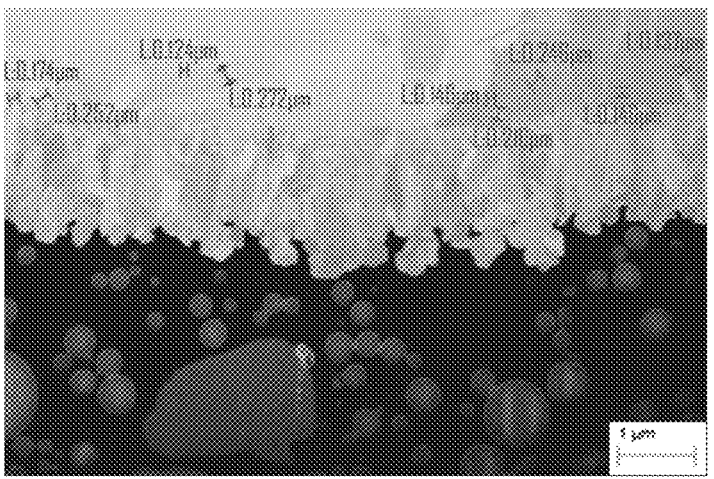

DETECTOR

INCIDENT ELECTRON BEAM

ND: Norml Direction

TD:
Transverse Direction

SAMPLE

70°

EBSD PATTERN

RD: Reference Direction

LAMINATE FOR WIRING BOARD

TECHNICAL FIELD

The present invention relates to laminates for wiring boards.

BACKGROUND ART

In recent years, demand for finer wiring has been increasing (JP-A-2005-223226). Wiring using a subtractive process, in which unnecessary copper portions are etched away using a conventional insulating resin with copper foils formed thereon, cannot meet the demand for finer wiring (JP-A-2010-267891). Therefore, wiring techniques such as semi-additive (SAP) and modified semi-additive (MSAP) processes are used. Compared to the subtractive process, the SAP process inherently produces a thinner copper film due to its operation mechanism, which enables finer wiring.

The MSAP process is a technique in which an ultra-thin copper foil on a carrier having a copper layer of several micrometers thick formed through a release layer on a support is used to form a seed layer on an insulating resin, and then copper is electrolytically plated as a thick layer on a pattern part formed by layering a resist, and then the resist and seed layer are removed to thereby form wiring (JP-A-2002-176242). Compared to the subtractive process, the MSAP process inherently produces a thinner copper film due to its operation mechanism, which enables finer wiring.

In the SAP process, the adhesive ability between a resin substrate and an electroless copper-plated film is enhanced by causing the resin to form protrusions that serve as anchors. For this, examples of the method of causing the resin to form protrusions that serve as anchors include roughening of the surface of the resin using a desmear technique such as a permanganate desmear process.

SUMMARY OF THE INVENTION

Problems to be Solved by the Invention

Thus, it is an object of the present invention to provide novel laminates for wiring boards.

Means to Solve the Problem

An aspect of the present invention is a laminate for wiring boards including an insulating substrate layer and copper wiring, the laminate having a circuit linearity of 1.0 or more and 1.7 or less. A seed layer may be present at a boundary between the insulating substrate layer and the copper wiring. The seed layer may have a thickness of 1.5 μm or smaller. Oxygen atoms may be detected in the seed layer in elemental mapping using an energy-dispersive X-ray spectroscope (EDS). Crystal grains of copper with a maximum width of 100 nm or larger may account for 1% or less relative to the total volume in the seed layer. A percentage of crystal grains with a maximum width of 500 nm or larger may be at least 0% and less than 50% when a size distribution of the crystal grains is measured using electron backscatter diffraction (EBSD) in the seed layer. A percentage of crystal grains with a maximum width of 50 nm or larger may be at least 0% and less than 50% when a size distribution of the crystal grains is measured using electron backscatter diffraction (EBSD) in the seed layer. Crystal grains with a maximum width of 500 nm or larger may not be detected when a size distribution of the crystal grains is measured using electron backscatter diffraction (EBSD) in the seed layer. Crystal grains with a maximum width of 50 nm or larger may not be detected when a size distribution of the crystal grains is measured using electron backscatter diffraction (EBSD) in the seed layer. The insulating substrate layer may have relative permittivity of 5.0 or less.

CROSS-REFERENCE TO RELATED DOCUMENTS

The present application claims priority to Japanese patent application No. 2021-052398, filed on Mar. 25, 2021, which is hereby incorporated by reference.

BRIEF DESCRIPTION OF THE DRAWINGS

FIG. 1A(A) illustrates a method for manufacturing laminates in an embodiment of the present invention in comparison with a MSAP process in a related art. (A-1) represents the MSAP process and (A-2) represents a method of this embodiment.

FIG. 1A(B) shows a scanning electron micrograph of a cross section made in an embodiment of the present invention in comparison with the one in a MSAP process in a related art. (B-1) is for the MSAP process and (B-2) is for a method of this embodiment.

FIG. 1B is a schematic diagram of seed layers in an embodiment of the present invention. The gray area represents an insulating substrate layer, and the black area represents a copper component that has been transferred to the insulating substrate layer. When the copper component is peeled off from the insulating substrate layer, (A) represents an example of a case where the copper component is peeled off just at the surface of the insulating substrate layer and (B) represents an example of a case where the copper component is peeled off at a position away from the surface of the insulating substrate layer, behind the protrusions and closer to the inside the copper component. The two straight lines correspond to the positions of: the surface of the copper component that has been peeled off, and a plane defined to include the bottom of the deepest recess formed in the insulating substrate layer by the protrusions of the copper component. The area sandwiched between these two straight lines is the seed layer, and the distance between the two lines denoted by the arrows corresponds to the thickness of the seed layer.

FIGS. 4-1 to 4-3 show results of ATR FT-IR measurement of surfaces of composite copper foils in the Examples 1-3 and the Comparative Examples 2-4 obtained after the copper foils were bonded to a resin substrate (R5670KJ) by thermocompression and peeled off from there;

FIG. 5 shows results of ATR FT-IR measurement of surfaces of composite copper foils in the Example 3 and the Comparative Example 3 obtained after the copper foils were bonded to a resin substrate (R1551GG) by thermocompression and peeled off from there;

FIGS. 6-1 and 6-2 show results of ATR FT-IR measurement of surfaces of composite copper foils in the Examples 4-8 obtained after the copper foils were bonded to a resin substrate (R5680J) by thermocompression and peeled off from there;

FIG. 7 shows results of ATR FT-IR measurement of surfaces of composite copper foils in the Example 3 and the Comparative Example 3 obtained after the copper foils were bonded to a resin substrate (NX9255) by thermocompression and peeled off from there;

FIG. 9 represents results of elemental mapping performed by an energy dispersive X-ray spectroscope (EDS) on cross sections of laminates in the Example [2] of the present invention.

FIG. 11 depicts SEM images of laminates manufactured using composite copper foils of Example 9 and Comparative Example 5.

EMBODIMENTS FOR CARRYING OUT THE INVENTION

Figures 1, 3:
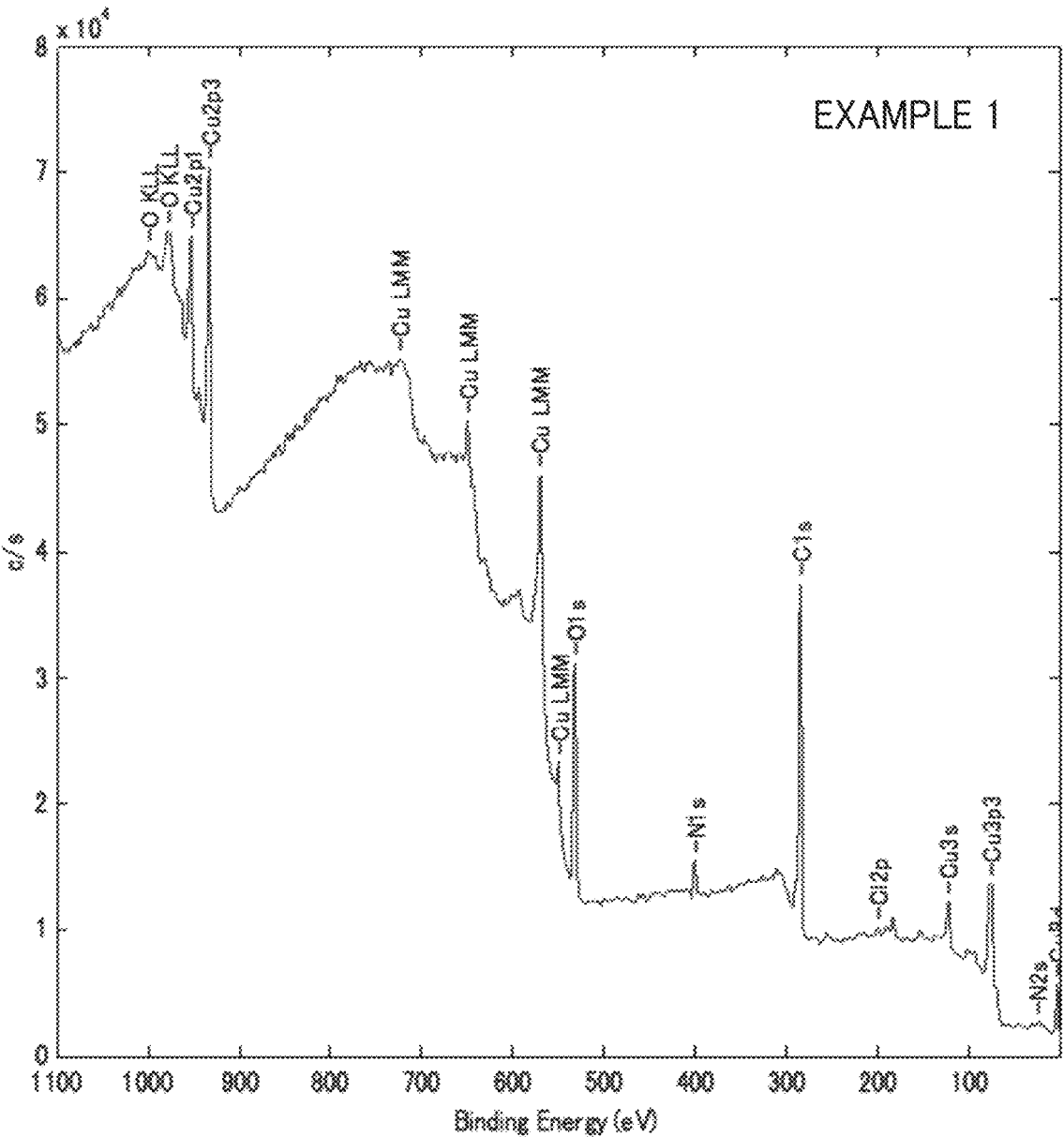
FIGS. 3-1 to 3-7 show results of XPS analysis of the resin substrates in the Examples 1-3 and the Comparative Examples 1-4.

Preferred embodiments of the present invention are described in detail below with reference to the attached drawings, but the present invention is not limited thereto. Objects, characteristics, advantages, and ideas of the present invention are apparent to a person skilled in the art from the description of the present specification, and a person skilled in the art can easily reproduce the present invention from the description of the present specification. Modes for carrying out the invention, specific examples thereof and so forth, which are described below, provide preferable embodiments of the present invention. They are described for the purpose of illustration or explanation, and thus the present invention is not limited thereto. It is apparent to a person skilled in the art that various alterations and modifications can be made on the basis of the description of the present specification within the spirit and the scope of the present invention disclosed in the present specification.

<Insulating Substrate Layer and Copper Laminate>

An embodiment of the disclosure of the present specification is a laminate for wiring boards including an insulating substrate layer and copper wiring, the laminate having a circuit linearity (i.e., a value of the ratio of the total length of one side edge of the copper wiring in the longitudinal direction on the surface where the copper wiring contacts the insulating substrate layer to the length of the copper wiring in the longitudinal direction; the closer the copper wiring is to be straight with fewer irregularities on the surface where the copper wiring contacts the insulating substrate layer, the closer the value of the ratio to 1.0) of 1.0 or more and 1.7 or less, preferably 1.5 or less, and more preferably 1.4 or less, and even more preferably 1.36 or less. For example, a circuit with a value of this ratio closer to 1.0 has a better linearity and a shorter transmission path, with a smaller transmission loss. In contrast, the larger the difference between 1.0 and the value of the ratio, the poorer the linearity of the circuit, the longer the transmission path, and the larger the transmission loss, especially in a high frequency range.

This laminate for wiring boards has a seed layer formed by embedding a metal derived from a copper component in recesses formed in the surface of the insulating substrate layer. It is desirable that oxygen atoms be detected in the seed layer in elemental mapping using an energy dispersive X-ray spectroscope (EDS). This is because copper oxides have an extremely low conductivity, and thus make it difficult for electricity to flow when they are present in the seed layer, resulting in almost no transmission loss due to the presence of the seed layer. In this specification, the seed layer refers to a layer formed between the surface of the copper component that has been peeled off and a plane defined to include the bottom of the deepest recess formed in the insulating substrate layer by the protrusions of the copper component (FIG. 1B). Thus, the recesses and the metal derived from the copper component that has been transferred to the recesses are included in that layer. The bottom of the deepest recess is one of the bottoms of the plurality of recesses which is furthest from the surface of copper component that has been peeled off. The plane defined to include the bottom of the deepest recess is parallel to the surface of the copper component that has been peeled off.

For this laminate for wiring boards, an etch factor is preferably 3.65 or higher in the Examples, more preferably 3.70 or higher, yet more preferably 3.75 or higher, and still more preferably 3.80 or higher. The smaller the etch factor, the larger the difference between the widths of the upper and lower sides (the width of the lower side minus the width of the upper side) with respect to the cross-sectional shape of the laminate. If the width of the bottom base is shortened for miniaturization, the width of the top base cannot be maintained. Therefore, a larger etch factor is preferable for finer wiring.

The crystalline state of the copper in the seed layer of this laminate for wiring boards is preferably uniform. This facilitates the control of the etch rate and enables the stable formation of wiring. For example, when the size distribution of the crystal grains is measured using electron backscatter diffraction (EBSD), it is preferable that the percentage of crystal grains with the maximum width of 500 nm or larger which are present in the seed layer is at least 0% and less than 50%, more preferably at least 0% and less than 10%, and yet more preferably at least 0% and less than 1%. Alternatively, it is preferable that the percentage of crystal grains with the maximum width of 300 nm or larger which are present in the seed layer is at least 0% and less than 50%, more preferably at least 0% and less than 10%, and yet more preferably at least 0% and less than 1%. Alternatively, it is preferable that the percentage of crystal grains with the maximum width of 100 nm or larger which are present in the seed layer is at least 0% and less than 50%, more preferably at least 0% and less than 10%, and yet more preferably at least 0% and less than 1%. Alternatively, it is preferable that the percentage of crystal grains with the maximum width of 50 nm or larger which are present in the seed layer is at least 0% and less than 50%, more preferably at least 0% and less than 10%, and yet more preferably at least 0% and less than 1%. Here, the percentage of crystal grains of a certain size of 0% means that no crystal grain of that size can be detected. When the size distribution of the crystal grains is measured using electron backscatter diffraction (EBSD), it is preferable that no crystal grain of 500 nm or larger can be detected in the seed layer; it is more preferable that no crystal grain of 200 nm or larger can be detected; it is yet more preferable that no crystal grain of 100 nm or larger can be detected; and it is still more preferable that no crystal grain of 50 nm or larger can be detected. Alternatively, when the crystal structure is observed using a scanning electron microscope (SEM) based on the contrast between brightness and darkness reflecting the crystal orientation, the seed layer contains only 0% to 1%, preferably 0% to 0.3%, more preferably 0% to 0.1% of crystal grains of copper with a maximum width of 100 nm or larger relative to the total volume. In turn, on the copper wiring side, crystal grains with a maximum width of 100 nm or larger are present in an amount of 5% or more relative to the total volume. Contrary to these cases, if the crystalline state is not uniform, it is difficult to control the etch rate, and problems such as over-etching, incompletely-etched residues, and undercuts may occur during circuit formation.

<Method for Manufacturing Laminates>

One embodiment of the disclosure of the present specification is a method for manufacturing a laminate of an insulating substrate layer and copper, comprising the steps of: bonding the insulating substrate layer and a copper component having protrusions on its surface; transferring the protrusions to the surface of the insulating substrate layer by peeling off the copper component to form a seed layer; forming a resist at a predetermined position on the surface of the seed layer; copper-plating the surface of the seed layer in an area where the resist has not been layered to laminate the copper; removing the resist; and removing the seed layer that has been exposed by the removal of the resist.

[1] Bonding of an Insulating Substrate Layer and a Copper Component

<Copper Component>

The copper component has fine protrusions on its surface.

The arithmetic mean roughness (Ra) of the surface of the copper component is preferably 0.03 µm or more, more preferably 0.05 µm or more, and is preferably 0.3 µm or less, and more preferably 0.2 µm or less.

The maximum height roughness (Rz) of the surface of the copper component is preferably 0.2 µm or more, more preferably 1.0 µm or more, and is preferably 2.0 µm or less, and more preferably 1.7 µm or less.

When Ra and Rz are too small, adhesion to the resin substrate will be insufficient, and when they are too large, fine wiring formability and high-frequency characteristics will be inferior.

Here, the arithmetic mean roughness (Ra) is the average of absolute values of $Z(x)$ (i.e., peak heights and valley depths) on a profile curve $(y=Z(x))$ within a reference length 1, expressed by the following equation.

$$Ra = \frac{1}{l} \int_0^l |Z(x)| dx \qquad \text{[Equation 1]}$$

The maximum height roughness (Rz) is the sum of the maximum values of peak height Zp and valley depth Zv of the profile curve $(y=Z(x))$ within the reference length 1.

Ra and Rz can be calculated using the specified method in JIS B 0601:2001 (in accordance with the international standard ISO 4287-1997).

The surface of the copper component has a mean width (RSm) of any value, of the roughness curve elements, but the mean width is preferably 1500 nm or smaller, 1400 nm or smaller, 1300 nm or smaller, 1200 nm or smaller, 1100 nm or smaller, 1000 nm or smaller, 900 nm or smaller, 800 nm or smaller, 750 nm or smaller, 700 nm or smaller, 650 nm or smaller, 600 nm or smaller, 550 nm or smaller, 450 nm or smaller, or 350 nm or smaller, and is more preferably 100 nm or larger, 200 nm or larger, or 300 nm or larger. As used herein, RSm is the average of the spacings (i.e., the widths of profile curve elements: $X_{s1}$, to $X_{sm}$) of the profile containing one profile peak and one valley over the roughness curve within a certain reference length (Ir) and is calculated by the following formula.

$$RSm = \frac{1}{m} \sum_{i=1}^{m} Xsi \qquad \text{[Equation 2]}$$

Here, the spacing of the profile containing one peak and one valley is defined with 10% of the arithmetic mean roughness (Ra) as the minimum height discrimination for the protrusions, and 1% of the reference length (lr) as the minimum length. For example, RSm can be measured and calculated according to "Test method for surface roughness of fine ceramic films by atomic force microscopy" (JIS.R 1683:2007).

It is preferable that the copper component includes a copper oxide-containing layer formed on at least a portion of its surface. Specific examples of the copper component include, but are not limited to, copper foils such as electrolytic copper foils, rolled copper foils, and copper foils laid on a carrier; copper wires; copper plates; and copper lead frames. The copper component contains, as the main component, copper (Cu) that constitutes a part of a structure. The copper component preferably consists of pure copper with Cu purity of 99.9% or higher by mass. It is more preferable if the copper component is made of tough pitch copper, deoxidized copper, or oxygen-free copper. It is even more preferable if the copper component is made of oxygen-free copper with oxygen content of 0.001% to 0.0005% by mass.

When the copper component is a copper foil, its thickness can have any value. The thickness, however, is preferably from 0.1 µm to 100 µm, and more preferably from 0.5 µm to 50 µm.

<Method of Producing Copper Components>

The copper oxide-containing layer, which is formed on the surface of the copper component, comprises copper oxide (CuO) and/or cuprous oxide (Cu₂O). This copper oxide-containing layer can be formed by oxidizing the surface of the copper component, and such oxidation roughens that surface of the copper component.

No roughening process such as soft etching or etching is necessary before the oxidation process, but roughing may be performed. Before the oxidation treatment, degreasing, acid cleaning to remove any natural oxide film for making the surface uniform, or alkali treatment to prevent acids from being introduced into the oxidation process after acid cleaning may be performed. Any method of alkali treatment can be used, but the treatment may be performed at 30° C.-50°

C. for about 0.5-2 minutes using an alkaline solution such as an aqueous solution of sodium hydroxide of preferably 0.1-10 g/L, more preferably 1-2 g/L.

Any oxidizing agent can be used, such as an aqueous solution of sodium chlorite, sodium hypochlorite, potassium chlorate, or potassium perchlorate. Various additives (e.g., phosphates such as trisodium phosphate dodecahydrate) or a surface-active molecule may be added to the oxidizing agent. Examples of the surface-active molecule include porphyrin, porphyrin macrocycles, expanded porphyrins, sub-porphyrins, linear porphyrin polymers, porphyrin sandwich complexes, porphyrin arrangements, silane, tetraorgano-silane, aminoethyl-aminopropyl-trimethoxysilane, (3-aminopropyl)trimethoxysilane, (1-[3-(trimethoxysilyl) propyl]urea) ((1-[3-(trimethoxysilyl)propyl]urea)), (3-aminopropyl)triethoxysilane, ((3-glycidyl-oxypropyl) trimethoxysilane), (3-chloropropyl)trimethoxysilane, (3-glycidyl-oxypropyl)trimethoxysilane, dimethyldichlorosilane, 3-(trimethoxysilyl)propylmethacrylate, ethyltriacetoxysilane, triethoxy(isobutyl)silane, triethoxy(octyl)silane, tris(2-methoxyethoxy)(vinyl)silane, chlorotrimethylsilane, methyltrichlorosilane, silicon tetrachloride, tetraethoxysilane, phenyltrimethoxysilane, chlorotriethoxysilane, ethylene-trimethoxysilane, amines, and sugars. Any conditions can be used for the oxidation reaction, but the temperature of the solution used for oxidation is preferably 40° C.-95° C., and more preferably 45° C.-80° C. The reaction time is preferably 0.5-30 minutes, and more preferably 1-10 minute(s).

Protrusions on the oxidized surface of the copper component may be modified by exposing the copper oxide-containing layer to a dissolving agent. Any dissolving agent can be used for this dissolving process, but the dissolving agent is preferably a chelating agent, especially a biodegradable chelating agent. Examples include ethylenediaminetetraacetic acid, diethanolglycine, tetrasodium L-glutamate diacetate, ethylenediamine-N,N'-disuccinic acid, 3-hydroxy-2,2'-iminodisuccinic acid sodium, methyl glycine diacetic acid trisodium, tetrasodium aspartate diacetate, N-(2-hydroxyethyl) iminodiacetic acid disodium, and sodium gluconate. The dissolving solution may have any pH, but the pH is preferably alkaline, more preferably between 8 and 10.5, still more preferably between 9.0 and 10.5, and yet more preferably between 9.8 and 10.2.

The surface of the copper oxide-containing layer may be reduced using a reducing agent. In such a case, cuprous oxide may be formed on the surface of the copper oxide-containing layer. Examples of the reducing agent used for this reducing process include dimethylamine borane (DMAB), diborane, sodium borohydride, and hydrazine.

The specific resistance of pure copper is $1.7 \times 10^{-8}$ ($\Omega$m), whereas that of copper oxide is 1-10 ($\Omega$m) and that of cuprous oxide is $1 \times 10^6$ to $1 \times 10^7$ ($\Omega$m). Thus, the copper oxide-containing layer has low conductivity. This means that transmission losses due to the skin effect are unlikely to occur for circuits on a printed wiring board or a semiconductor package substrate formed using a copper component according to the present invention, even when a larger amount of the copper oxide-containing layer has been transferred to a resin substrate.

Each copper oxide-containing layer may contain metal other than copper. Any metal can be included, but the copper oxide-containing layer may contain at least one metal selected from the group consisting of Sn, Ag, Zn, Al, Ti, Bi, Cr, Fe, Co, Ni, Pd, Au, and Pt. In particular, to exhibit acid and heat resistance, the copper oxide-containing layer preferably contains metal having a higher acid resistance and heat resistance than copper, such as Ni, Pd, Au, and Pt.

A layer containing metal other than copper can be formed on top of the copper oxide-containing layer. This layer can be formed on the top surface of the copper component by plating. Any plating technique can be used, such as electrolytic plating, electroless plating, vacuum deposition, or conversion treatment, using metal such as Sn, Ag, Zn, Al, Ti, Bi, Cr, Fe, Co, Ni, Pd, Au, or Pt, or other various alloys as the metal other than copper. Electrolytic plating, however, is preferred because it is desirable to form a uniform and thin plated layer.

For electrolytic plating, nickel plating and nickel alloy plating are preferred. Examples of metal that is deposited by nickel plating and nickel alloy plating include pure nickel, Ni—Cu alloys, Ni—Cr alloys, Ni—Co alloys, Ni—Zn alloys, Ni—Mn alloys, Ni—Pb alloys, and Ni—P alloys.

Examples of metal salts used for plating include nickel sulfate, nickel sulfamate, nickel chloride, nickel bromide, zinc oxide, zinc chloride, diamminedichloropalladium, iron sulfate, iron chloride, chromic anhydride, chromium chloride, sodium chromium sulfate, copper sulfate, copper pyrophosphate, cobalt sulfate, and manganese sulfate.

In nickel plating, a preferable bath composition includes, for example, nickel sulfate (100 g/L or more and 350 g/L or less), nickel sulfamate (100 g/L or more and 600 g/L or less), nickel chloride (0 g/L or more and 300 g/L or less), and mixtures thereof. Sodium citrate (0 g/L or more and 100 g/L or less) or boric acid (0 g/L or more and 60 g/L or less) may be included as an additive.

When an oxidized copper foil surface is electrolytically plated, the copper oxide on the surface is first reduced to cuprous oxide or pure copper. This consumes electrical charges, resulting in a time delay before the completion of plating, and subsequently, the metal that forms a metal layer begins to deposit. The amount of charge depends on the type of plating solution and the amount of copper oxide used. For example, when a copper component is plated with nickel, it is preferable to apply a charge ranging from 10 C to 90 C per dm of area of the copper component to be electrolytically plated, and it is more preferable to apply a charge ranging from 20 C to 65 C, in order to keep the thickness of the nickel plating within a desirable range.

The amount of metal adhered on the outermost surface of the copper component by plating is not limited, but is preferably 0.8-6.0 mg/dm$^2$. The amount of adhered metal can be calculated, for example, by dissolving the metal in an acidic solution, measuring the amount of metal by ICP analysis, and dividing that amount by the projected area of the structure.

To facilitate tearing off of the copper oxide-containing layer from the copper component, the following processes may be used: 1) partially coating the surface of the copper component with a coating agent such as a silane coupling agent or an anti-erosion agent before an oxidation treatment; or 2) treating the copper oxide-containing layer with a dissolving agent after the oxidation treatment. By partially coating the surface of the copper component with a coating agent such as a silane coupling agent or an anti-erosion agent, the coated area is spared from being subjected to oxidation and voids are created in the copper oxide-containing layer, making it easier for the copper oxide-containing layer to break away or torn off from the copper component. Here, the term "dissolving agent" refers to an agent that dissolves or erodes copper oxides. The treatment with a dissolving agent partially erodes the copper oxide near the boundary between the copper component and the copper oxide-containing layer, making it easier for the copper oxide-containing layer to leave from the copper component.

Any silane coupling agent can be used, and one may be selected from silane, tetraorgano-silane, aminoethyl-aminopropyl-trimethoxysilane, (3-aminopropyl)trimethoxysilane, (1-[3-(trimethoxysilyl)propyl]urea) ((1-[3-(trimethoxysilyl)propyl]urea)), (3-aminopropyl)triethoxysilane, ((3-glycidyloxypropyl)trimethoxysilane), (3-chloropropyl)trimethoxysilane, (3-glycidyl-oxypropyl)trimethoxysilane, dimethyldichlorosilane, 3-(trimethoxysilyl)propylmethacrylate, ethyltriacetoxysilane, triethoxy(isobutyl)silane, triethoxy(octyl)silane, tris(2-methoxyethoxy)(vinyl)silane, chlorotrimethylsilane, methyltrichlorosilane, silicon tetrachloride, tetraethoxysilane, phenyltrimethoxysilane, chlorotriethoxysilane, and ethylene-trimethoxysilane.

Any anti-corrosion agent can be used, and one may be selected from 1H-tetrazole, 5-methyl-1H-tetrazole, 5-amino-1H-tetrazole, 5-phenyl-1H-tetrazole, 1,2,3-triazole, 1,2,4-triazole, 1,2,3-benzotriazole, 5-methyl-1H-benzotriazole, 5-amino-1H-benzotriazole, 2-mercaptobenzothiazole, 1,3-dimethyl-5-pyrazolone, pyrrole, 3-methylpyrrole, 2,4-dimethylpyrrole, 2-ethylpyrrole, pyrazole, 3-aminopyrazole, 4-methylpyrazole, 3-amino-5-hydroxypyrazole, thiazole, 2-aminothiazole, 2-methylthiazole, 2-amino-5-methylthiazole, 2-ethylthiazole, benzothiazole, imidazole, 2-methylimidazole, 2-ethylimidazole, 2-butylimidazole, 5-aminoimidazole, 6-aminoimidazole, benzimidazole, and 2-(methylthio)benzimidazole.

Treatment with a silane coupling agent or an anti-erosion agent may be performed at any time prior to the oxidation, and may be performed in conjunction with degreasing, acid cleaning to remove any natural oxide film for uniform treatment, or alkaline treatment to prevent acids from being introduced into the oxidation process after acid cleaning.

For the treatment with a silane coupling agent or an anti-erosion agent, it is preferable that the surface of the copper component is partially (e.g., 1%, 5%, 10%, 20%, 30%, 40%, 50%, 60%, 70%, 80%, 90% or more, but less than 100%) coated. For this purpose, it is preferable to allow it to react at a concentration of 0.1%, 0.5%, 1% or 2% or more for 30 seconds, 1 minute, or 2 minutes or more at room temperature.

Any dissolving agent can be used for facilitating the tearing off of the copper oxide-containing layer from the copper component, as long as the dissolving agent contains an ingredient that dissolves copper oxide. The dissolving agent is not limited to nickel chloride and may be selected from chlorides (e.g., potassium chloride, zinc chloride, iron chloride, and chromium chloride), ammonium salts (e.g., ammonium citrate, ammonium chloride, ammonium sulfate, ammonium chloride, nickel ammonium sulfate), chelating agents (e.g., ethylenediaminetetraacetic acid, diethanolglycine, tetrasodium L-glutamate diacetate, ethylenediamine-N,N'-disuccinic acid, 3-hydroxy-2,2'-iminodisuccinic acid sodium, methyl glycine diacetic acid trisodium, tetrasodium aspartate diacetate, N-(2-hydroxyethyl)iminodiacetic acid disodium, and sodium gluconate), tin(II) chloride, and citric acid.

For treatments with nickel chloride, it is preferable, but not limited, to immerse the copper component with the copper oxide-containing layer formed thereon in a nickel chloride solution (at a concentration of 45 g/L or more) for 5 seconds or more at room temperature or a higher temperature. Other than the treatment with nickel chloride alone, it may also be performed at the same time as oxidation treatment, or after oxidation treatment and at the same time as plating treatment. For example, nickel chloride may be contained in a plating bath and, and the copper component with the copper oxide-containing layer formed thereon may be immersed in the plating bath for 5, 10, 15, 20, or 30 seconds or 1 minute, or 2 minutes before plating. The time of immersion can vary as necessary depending on, for example, the thickness of an oxidized film.

<Insulating Substrate Layer>

Any substrate can be used for the insulating substrate layer as long as the surface profile of a copper component including its surface topology with protrusions and troughs is imprinted onto the resin substrate when the surface of the copper component with concavities and convexities is bonded to the insulating substrate layer, but a resin substrate is preferred. The resin substrate is a material that comprises resin as a main component. Any type of resins can be used, and the resin may be either thermoplastic or thermosetting. Examples of the resin include polyphenylene ether (PPE), epoxy, polyphenylene oxide (PPO), polybenzoxazole (PBO), polytetrafluoroethylene (PTFE), a liquid crystal polymer (LCP), triphenylphosite (TPPI), a fluoropolymer, polyetherimide, polyetheretherketone, polycycloolefin, a bismaleimide resin, low dielectric constant polyimide, a cyanate resin, or their mixed resin. The resin substrate may also contain inorganic fillers and/or glass fibers. The relative permittivity of the insulating substrate layer used is preferably 5.0 or less, more preferably 4.0 or less, and yet more preferably 3.8 or less.

<Bonding>

When the surface of the copper component with concavities and convexities is bonded to the insulating substrate layer, the surface profile of the copper component including its surface topology with protrusions and troughs is imprinted onto the resin substrate. Therefore, peaks and valleys complementary to the valleys and peaks, respectively, in and on the surface of the copper component are formed on and in the surface of the insulating substrate layer.

Although any bonding method can be used, it is preferable to use thermocompression bonding (thermal press fitting). The resin substrate can be bonded to the surface of the copper component by thermocompression by, for example, laminating the resin substrate on the copper component in close contact to each other, and then thermally treating them under given conditions. As to the given conditions (e.g., temperature, pressure, and time), conditions recommended by each substrate manufacturer may be used. For example, the following conditions can be considered as the given conditions.

1) If the resin substrate contains or consists of an epoxy resin, the copper component is bonded to the resin substrate by thermocompression preferably by applying a pressure ranging from 0-20 MPa at a temperature of 50° C.-300° C. for 1 minute to 5 hours.

For example, 1-1) when the resin substrate is R-1551 (manufactured by Panasonic Corp.), the copper component is subjected to thermocompression bonding by heating it at a pressure of 1 MPa; after the temperature reaches 100° C., holding it at this temperature for 5-10 minutes; subsequently, further heating it at a pressure of 3.3 MPa; and, after the temperature reaches 170-180° C., holding it at this temperature for 50 minutes;

1-2) when the resin substrate is R-1410A (manufactured by Panasonic Corp.), the copper component is subjected to thermocompression bonding by heating it at a pressure of 1 MPa; after the temperature reaches 130° C., holding it at this temperature for 10 minutes; subsequently, further heating it at a pressure of 2.9

MPa; and, after the temperature reaches 200° C., holding it at this temperature for 70 minutes;

1-3) when the resin substrate is EM-285 (manufactured by EMC), the copper component is subjected to thermocompression bonding by heating it at a pressure of 0.4 MPa; after the temperature reaches 100° C., further heating it under an increased pressure of 2.4-2.9 MPa; and, after the temperature reaches 195° C., holding it at this temperature for 50 minutes; or 1-4) when the resin substrate is GX13 (manufactured by Ajinomoto Fine-Techno Co., Inc.), the copper component is subjected to thermocompression bonding by heating it while applying a pressure of 1.0 MPa; and holding it at 180° C. for 60 minutes.

2) If the resin substrate contains or consists of a PPE resin, the copper component is bonded to the resin substrate by thermocompression preferably by applying a pressure ranging from 0 to 20 MPa at a temperature of 50° C.-350° C. for 1 minute to 5 hours.

For example, 2-1) when the resin substrate is R5620 (manufactured by Panasonic Corp.), the copper component is subjected to thermocompression bonding by heating it at a pressure of 0.5 MPa until the temperature reaches 100° C.; and subsequently, it is further subjected to thermocompression bonding by increasing the temperature and pressure, and holding it at 2.0-3.0 MPa and 200° C.-210° C. for 120 minutes;

2-2) when the resin substrate is R5670 (manufactured by Panasonic Corp.), the copper component is subjected to thermocompression bonding by heating it at a pressure of 0.49 MPa until the temperature reaches 110° C.; and subsequently, it is further subjected to thermocompression bonding by increasing the temperature and pressure, and holding it at 2.94 MPa and 210° C. for 120 minutes;

2-3) when the resin substrate is R5680 (manufactured by Panasonic Corp.), the copper component is subjected to thermocompression bonding by heating it at a pressure of 0.5 MPa until the temperature reaches 110° C.; and subsequently, it is further subjected to thermocompression bonding by increasing the temperature and pressure, and holding it at 3.0-4.0 MPa and 195° C. for 75 minutes; or 2-4) when the resin substrate is N-22 (manufactured by Nelco), the copper component is subjected to thermocompression bonding by heating it while applying a pressure of 1.6-2.3 MPa; holding it at 177° C. for 30 minutes; subsequently, further heating it; and holding it at 216° C. for 60 minutes.

3) If the resin substrate contains or consists of a PTFE resin, the copper component is bonded to the resin substrate by thermocompression preferably by applying a pressure ranging from 0 to 20 MPa at a temperature of 50° C.-400° C. for 1 minute to 5 hours.

For example, 3-1) when the resin substrate is NX9255 (manufactured by Park Electrochemical Corp.), the copper component is subjected to thermocompression bonding by heating it while applying a pressure of 0.69 MPa until the temperature reaches 260° C.; increasing the pressure to 1.03-1.72 MPa and heating the copper component up to 385° C.; and holding it at 385° C. for 10 minutes; or 3-2) when the resin substrate is R03003 (manufactured by Rogers Corp.), the copper component is subjected to thermocompression bonding by applying a pressure to 2.4 MPa after the elapse of 50 minutes (approximately 220° C.) from the beginning of press; and holding the copper component at 371° C. for 30-60 minutes.

4) If the resin substrate contains or consists of a liquid crystal polymer (LPC), the copper component is bonded to the resin substrate by thermocompression preferably by applying a pressure ranging from 0 to 20 MPa at a temperature of 50° C.-400° C. for 1 minute to 5 hours. For example, when the resin substrate is CT-Z (manufactured by Kuraray Co., Ltd.), the copper component is subjected to thermocompression bonding by heating it at a pressure of 0 MPa, holding it at 260° C. for 15 minutes, further heating it while applying a pressure of 4 MPa, and holding it at 300° C. for 10 minutes.

[2] Peeling Off the Copper Component

When the copper component is peeled off from the insulating substrate layer under given conditions after the copper component is bonded to the insulating substrate layer, the protrusions on the surface of the copper component are transferred to the insulating substrate layer to form a seed layer on the surface of the insulating substrate layer. Therefore, the surface of the insulating substrate layer becomes flat.

It is sufficient if the thickness of the seed layer is 2.50 μm or smaller, but the thickness is preferably 2.00 μm or smaller, and more preferably 1.70 μm or smaller. In addition, the thickness is preferably 0.01 μm or larger, more preferably 0.10 μm or larger, and yet more preferably 0.36 μm or larger. The thickness of smaller than 0.01 μm results in poor plating formability and reduced adhesion to the insulating substrate. The thickness of larger than 2.50 μm results in poor wiring formability. Any method can be used to measure the thickness of the seed layer. For example, the thickness of the seed layer can be measured on the SEM image.

In the method of the present disclosure, the seed layer made in this way is used as it is as a part of a circuit. By omitting the process of removing the protrusions on the surface of the copper component transferred to the insulating substrate layer, good adhesion is achieved between the copper and the insulating substrate layer.

Any conditions can be used for peeling off the copper component from the insulating substrate layer, such as on the basis of a 900 peeling test (Japanese Industrial Standard (JIS) C5016 "Test methods for flexible printed wiring boards" corresponding international standards IEC249-1: 1982 and IEC326-2:1990). Any method can be used to remove the copper component from the insulating substrate layer. It may be performed by machine or by hand, i.e., manually.

The metal transferred to the surface of the insulating substrate layer after the copper component has been peeled off can be detected using various methods (e.g., X-ray photoelectron spectroscopy (XPS), energy-dispersive X-ray spectroscopy (EDS), or ICP optical emission spectroscopy (high-frequency inductively coupled plasma optical emission spectroscopy, ICP-OES/ICP-AES)). For example, the metal contained in the copper oxide-containing layer is transferred to the insulating substrate layer after the copper component with the copper oxide-containing layer on its surface has been peeled off.

XPS is a technique for energy analysis by irradiating an object with X-rays and capturing photoelectrons e emitted as the object is ionized. XPS can be used to determine the type, amount, and chemical bonding state of elements present on the surface of a sample or at a predetermined depth from the surface, e.g., up to a depth of 6 nm. The suitable diameter of an analysis spot (i.e., the diameter of the cross-section of a cylindrical part that can be analyzed when cut into a circle)

ranges from 1 μm to 1 mm. Here, it is sufficient if the metal atoms contained in the copper oxide-containing layer are detected, by XPS survey spectrum analysis, on the surface of the insulating substrate from which the copper component has been peeled off.

The metal contained in the protrusions of the copper component is preferably transferred to the insulating substrate layer such that it fills 70% or more, 80% or more, 90% or more, 95% or more, 99% or more, or 99.9% or more of the recesses in the imprinted surface profile. With most of the recesses in the insulating substrate layer being filled with metal, when the surface of the insulating substrate layer is measured using XPS, the sum of the intensities of main peaks of the spectra of metal atoms is preferably larger than the intensity of the main peak of C1s in the spectrum. The term "main peak" refers to a peak with the highest intensity among multiple peaks for each metal element. For example, the Cu 2p3, Sn 3d5, Ag 3d5, Zn 2p3, Al 2p, Ti 2p3, Bi 4f7, Cr 2p3, Fe 2p3, Co 2p3, Ni 2p3, Pd 3d5, Au 4f7, and Pt 4f7 orbitals correspond to the main peaks. The intensity of the peak in the spectrum here is the height in the direction of the vertical axis of the XPS spectral data.

The percentage of Cu2p3, measured by X-ray photoelectron spectroscopy (XPS), relative to the total number of atoms that are present in the surface of the insulating substrate layer from which the copper component has been peeled off, is preferably 1.0 atom % or more, 1.8 atom % or more, 2.8 atom % or more, 3.0 atom % or more, 4.0 atom % or more, 5.0 atom % or more, or 6.0 atom % or more. Alternatively, the ratio (in percentage) of Cu2p3/C1s in surface atomic composition is preferably 0.010 or more, 0.015 or more, 0.020 or more, 0.025 or more, 0.030 or more, 0.035 or more, 0.040 or more, 0.045 or more, 0.050 or more, or 0.10 or more, when the surface of the copper component after imprinting is measured by XPS.

If the protrusions of the copper component contain metal other than copper, a sum of percentages of metal atoms in atomic composition on the surface of the removed insulating substrate layer, as measured by X-ray photoelectron spectroscopy (XPS), is 1.0 atom % or more, 1.5 atom % or more, 1.8 atom % or more, 2.8 atom % or more, 3.0 atom % or more, 4.0 atom % or more, 5.0 atom % or more, or 6.0 atom % or more. Alternatively, a ratio of (a sum of percentages of metal atoms in atomic composition on the surface of the removed insulating substrate layer) to (a percentage of C1s in atomic composition on the surface of the removed insulating substrate layer) is preferably 0.010 or more, 0.015 or more, 0.020 or more, 0.025 or more, 0.030 or more, 0.035 or more, 0.040 or more, 0.045 or more, 0.050 or more, or 0.10 or more.

It is preferable that the amount of substance derived from the insulating substrate layer and detected on the surface of the copper component that has been peeled off from the insulating substrate layer is below the detection limit, or small even if detected. This shows that the breakage of the insulating substrate layer is sufficiently suppressed when the copper component is peeled off. Any method can be used to detect substances derived from the insulating substrate layer, and a method appropriate for the target substance can be used. For example, in the case of organic matter, it can be done by detecting the peak originating from the insulating substrate layer by attenuated total reflection Fourier transform infrared spectroscopy (FT-IR). ("Infrared and Raman Spectroscopy: Principles and Spectral Interpretation (by Peter Larkin)"). FT-IR is an infrared spectroscopy method that irradiates a target substance to be measured with infrared light and uses the infrared absorption spectrum to identify and/or quantify a compound. In a wavelength range of 700-4000 cm$^{-1}$, the signal-to-noise (S/N) ratio is preferably 10 or less, or 9 or less, and more preferably 8 or less, or 7 or less. It is preferable no peak derived from the resin substrate is detected.

The ratio of Ra after peeling to Ra before bonding on the surface of the copper component with the layer having protrusions formed thereon is preferably less than 100%, less than 96%, less than 95%, less than 94%, less than 93%, less than 92%, less than 91%, less than 90%, less than 80%, less than 70%, less than 65%, or less than 60%. The smaller percentage indicates that the more metal forming the layer having protrusions has been transferred to the insulating substrate layer.

The ratio of the surface area after peeling to the surface area before bonding of the copper component with the layer having protrusions formed thereon is preferably less than 100%, less than 98%, less than 97%, less than 96%, less than 95%, less than 94%, less than 93%, less than 92%, less than 91%, less than 90%, less than 80%, or less than 75%. The smaller percentage indicates that more metal forming the layer having protrusions has been transferred to the insulating substrate layer. The surface area can be measured using a confocal or atomic force microscope.

The ΔE*ab between the surface of the copper component before thermocompression bonding and the surface of the copper component after it was peeled off is preferably 13 or more, 15 or more, 20 or more, 25 or more, 30 or more, or 35 or more. The larger difference between them indicates that more metal forming protrusions has been transferred to an insulating resin substrate.

In conventional SAP processes, as described above, adhesion between a resin substrate and a seed layer is enhanced by causing the resin to form protrusions that serve as anchors. In this process, relatively large protrusions were formed on the surface to ensure adhesion. This, however, results in the precipitation of copper to a place deep from the surface layer of the resin, and thus a minute amount of copper was likely to remain upon etching away the seed layer. This minute amount of copper that had left could cause short-circuits among wiring, so that a deep etching process was required. Furthermore, an effect of increased adhesion by the formation of protrusions and electroless copper-plated film is highly selective to resin substrates, and sufficient adhesion can be obtained only in some resin substrates such as such as ABF (Ajinomoto Build-Up Film).

In conventional MSAP processes, an ultra-thin copper foil on a carrier is used. However, ultra-thin copper foil layers are required to have a thickness of at least 1.5 μm from the viewpoint of handling and so on. Besides, such layers have been subjected to roughening of at least 1 μm. By forming this roughened seed layer on the resin, the adhesion between a resin substrate and a seed layer is enhanced. In this process, it was necessary to remove a copper layer of several-micrometer thick including the ultra-thin copper foil layer and the roughened area. Thus, a deep etching process was required.

However, if a large amount of copper is etched for fine patterns used in recent years, some patterns may be damaged and lost by side etching. In addition, since wiring layers are formed on a roughened surface or on a seed layer including a roughened area of a resin substrate, transmission losses of high-frequency signals are likely to occur when there are large protrusions.

The seed layer obtained by the method of the present disclosure has a smaller surface roughness than that obtained by roughening through a desmear technique in the conventional SAP processes or by roughening an ultra-thin copper foil on a carrier in the conventional MSAP processes. Thus, it is possible to avoid problems such as residual copper after etching, damages of patterns by side etching in fine patterns, and transmission losses of high-frequency signals under the influence of the protrusions. Moreover, although the surface roughness is small, fine protrusions which are densely formed ensure sufficient adhesion between the insulating substrate and copper.

[3] Formation of a Resist at a Predetermined Position on the Surface of a Seed Layer After the copper component is peeled off, a resist is formed at a predetermined position on the surface of the seed layer. The place where the resist is formed is where the copper that will later become the circuit will not be laminated.

The resist may include, for example, a material that dissolves or cures by exposure and is preferably formed by, but not limited to, a dry film resist (DFR), positive liquid resist, or negative liquid resist.

The DFR preferably contains a binder polymer that contributes to film formability, and a monomer (e.g., acrylic ester or methacrylic ester monomer) that is photopolymerized upon exposure to UV and a photo-initiator. To form the DFR, it is preferable to use a dry film with a three-layer structure of cover-form/photoresist/carrier film. The DFR, which is a resist, can be formed on a structure by laminating the photoresist on the structure by thermocompression bonding while peeling off the cover film, and after the lamination, peeling off the carrier film.

Examples of liquid resists include novolac resins solubilized in organic solvents. For liquid resists, they can be applied to the surface of a structure, dried, and then irradiated with light to dissolve or cure the resist to form a resist.

The resist may have any thickness, but the thickness is preferably 1 μm to 200 μm.

After the seed layer is formed, the surface of the seed layer may be plated to form a second seed layer before the formation of a resist. Any plating method can be used, and plating may be either electrolytic or electroless plating. For example, one metal selected from among Ni, Sn, Al, Cr, Co, and Cu may be used and deposited as a film by a known electroless plating. Here, the second seed layer refers to a thin film of metal formed by plating. The second seed layer may have any thickness, and the thickness may be about 0.02-2 μm. It is, however, preferable that the thickness is 2.5 μm or less in total together with that of the seed layer on the surface of the insulating substrate layer.

[4] Copper Lamination

Next, the surface of the seed layer in an area where no resist has been layered is subjected to copper plating to laminate copper. This laminated copper will later function as a circuit.

Any method of copper plating can be used, and plating can be performed using a known method.

[5] Removal of the Resist

Any method can be used to remove the resist, and known methods can be used such as the one using fuming nitric acid or a sulfuric acid-hydrogen peroxide mixture, dry ashing using, for example, O₂ plasma.

[6] Removal of the Seed Layer

Any method can be used to remove the seed layer, and known methods can be used such as quick etching or flash etching using an etching agent based on sulfuric acid-hydrogen peroxide.

EXAMPLES

[1] Production of Laminated Samples

<1. Production of Composite Copper Foils>

In Examples 1-9 and Comparative Examples 2 and 3, a shiny side (a glossy side, which is flatter compared with the opposite side) of a copper foil (DR-WS, thickness: 18 μm), manufactured by FURUKAWA ELECTRIC CO., LTD., was used. In Comparative Example 4, a matte side of a copper foil (FV-WS, thickness: 18 μm), manufactured by FURUKAWA ELECTRIC CO., LTD., was used as a test piece without any treatment.

(1) Pretreatment

First, the copper foils were immersed in a solution described below at 25° C. for 1 minute:

in the Examples 1 and 2, 10 g/L of potassium carbonate and 1 vol. % of KBE-903 (3-aminopropyltriethoxysilane; manufactured by Shin-Etsu Silicone);

in the Example 3, 10 g/L of potassium carbonate and 0.06 g/L of potassium hydrogen carbonate;

in the Examples 4-6, 10 g/L of potassium hydroxide;

in the Example 7, 10 g/L of potassium hydroxide and 5 vol. % of KBM-603 (N-2-(aminoethyl)-3-aminopropyltrimethoxysilane; manufactured by Shin-Etsu Silicone);

in the Example 8, 10 g/L of potassium hydroxide and 1 wt. % of benzotriazole (BTA);

in the Comparative Example 2, a solution of 10 g/L of potassium carbonate; and in the Comparative Example 3, 0.06 g/L of potassium hydrogen carbonate and a solution of 10 g/L of potassium carbonate.

(2) Oxidation Treatment

The pretreated copper foils were immersed in an oxidizing agent for oxidation treatment.

In the Examples 1, 2, 7, and 8, and the Comparative Example 2, a solution of 60 g/L of sodium chlorite, 20.6 g/L of potassium hydroxide, and 40.2 g/L of potassium carbonate was used as an oxidizing agent.

In the Examples 3-6, a solution of 46.3 g/L of sodium chlorite, 12.3 g/L of potassium hydroxide, and 2.1 g/L of KBM-403 (3-glycidoxypropyltrimethoxysilane; manufactured by Shin-Etsu Silicone) was used as an oxidizing agent.

In the Comparative Example 3, a solution of 60.5 g/L of sodium chlorite, 9.1 g/L of potassium hydroxide, 3.1 g/L of potassium carbonate, and 2.1 g/L of KBM-403 (3-glycidoxypropyltrimethoxysilane; manufactured by Shin-Etsu Silicone) was used as an oxidizing agent.

The copper foils in the Examples 1, 2, 7, and 8 were immersed in the oxidizing agent at 73° C. for 6 minutes. Those in the Examples 3-6 and the Comparative Examples 2 and 3 were immersed in the oxidizing agent at 73° C. for 2 minutes.

(3) Plating Pretreatment

After the oxidation treatment, plating pretreatment was performed in the Examples 4-6 using dissolving agents as follows.

The copper foil in the Example 4 was treated using a solution of 47.2 g/L of tin(II) chloride dihydrate and 1 mL/L of hydrochloric acid at 45° C. for 10 seconds. The copper foil in the Example 5 was treated using a solution of 47.2 g/L of ammonium chloride at 45° C. for 60 seconds.

The copper foil in the Example 6 was treated using a solution of 6.5 mL/L of 50% citric acid at 45° C. for 60 seconds.

(4) Electrolytic Plating

After the oxidation treatment, in the Examples 2 and 3 and the Comparative Example 3, electrolytic plating was performed using a first electrolytic nickel-plating solution (255 g/L of nickel sulfate, 49 g/L of nickel chloride, and 20 g/L of sodium citrate). After the plating pretreatment, in the Examples 4-6, electrolytic plating was performed using a second electrolytic nickel-plating solution (255 g/L of nickel sulfate, and 20 g/L of sodium citrate). The copper foil in the Example 3 was immersed in an electrolytic nickel-plating solution for 1 minute before electrolytic plating. In the Example 2, the electrolytic plating was performed at 50° C. and a current density of 0.5 A/dm$^2$×116 s (=58 C/dm$^2$ copper foil area). In the Examples 3-6, and the Comparative Example 3, the electrolytic plating was performed at 50° C. and a current density of 0.5 A/dm$^2$×45 s (=22.5 C/dm$^2$ copper foil area).

For each of the Examples and the Comparative Examples, multiple test specimens were produced under the same conditions mentioned above. These conditions are summarized in Table 1.

the Examples 1-8 and the Comparative Examples 2-4 to conduct peel tests of the resin substrates.

First, each prepreg was laminated to the test specimens, which were bonded by thermocompression under vacuum using a vacuum high-pressure press machine to obtain laminated samples. When the resin substrate was R5670KJ (manufactured by Panasonic Corp.), the sample was subjected to thermocompression bonding while heating it at a pressure of 0.49 MPa until the temperature reached 110° C.; subsequently, the temperature and pressure were increased, and the sample was subjected to thermocompression bonding by holding it at 2.94 MPa and 210° C. for 120 minutes. When the resin substrate was R5680J (manufactured by Panasonic Corp.), the sample was subjected to thermocompression bonding while heating it at a pressure of 0.5 MPa until the temperature reached 110° C.; subsequently, the temperature and pressure were increased, and the sample was subjected to thermocompression bonding by holding it at 3.5 MPa and 195° C. for 75 minutes. When the resin substrate was NX9255 (Park Electrochemical Corp.), the sample was subjected to thermocompression bonding by

TABLE 1

| Treatment | Details | Components or conditions | Unit | Examples 1 | 2 | 3 | 4 | 5 | 6 | 7 | 8 | Comparative Examples 2 | 3 | 4 |
|---|---|---|---|---|---|---|---|---|---|---|---|---|---|---|
| PS | Composition | potassium carbonate | g/L | 10 | 10 | 10 | 0 | 0 | 0 | 0 | 0 | 10 | 10 | — |
| | | potassium hydrogen carbonate | g/L | 0 | 0 | 0.06 | 0 | 0 | 0 | 0 | 0 | 0 | 0.06 | — |
| | | potassium hydroxide | g/L | 0 | 0 | 0 | 10 | 10 | 10 | 10 | 10 | 0 | 0 | — |
| | | KBM-603 | vol. % | 0 | 0 | 0 | 0 | 0 | 0 | 5 | 0 | 0 | 0 | — |
| | | BTA | wt. % | 0 | 0 | 0 | 0 | 0 | 0 | 0 | 1 | 0 | 0 | — |
| | | KBE-903 | vol. % | 1 | 1 | 0 | 0 | 0 | 0 | 0 | 0 | 0 | 0 | — |
| | Treatment | Temp. | ° C. | 25 | 25 | 25 | 25 | 25 | 25 | 25 | 25 | 25 | 25 | — |
| | | Time | min. | 1 | 1 | 1 | 1 | 1 | 1 | 1 | 1 | 1 | 1 | — |
| AS | Composition | sodium chlorite | g/L | 60 | 60 | 46.3 | 46.3 | 46.3 | 46.3 | 60 | 60 | 60 | 60.5 | — |
| | | potassium hydroxide | g/L | 20.6 | 20.6 | 12.3 | 12.3 | 12.3 | 12.3 | 20.6 | 20.6 | 20.6 | 9.1 | — |
| | | potassium carbonate | g/L | 40.2 | 40.2 | 0 | 0 | 0 | 0 | 40.2 | 40.2 | 40.2 | 3.1 | — |
| | | KBM-403 | g/L | 0 | 0 | 2.1 | 2.1 | 2.1 | 2.1 | 0 | 0 | 0 | 2.1 | — |
| | Treatment | Temp. | ° C. | 73 | 73 | 73 | 73 | 73 | 73 | 73 | 73 | 73 | 73 | — |
| | | Time | min. | 6 | 6 | 2 | 2 | 2 | 2 | 6 | 6 | 2 | 2 | — |
| Pretreatment for Plating | Composition | tin(II) chloride, dihydrate | g/L | — | — | — | 47.2 | 0 | 0 | — | — | — | — | — |
| | | ammonium chloride | g/L | — | — | — | 0 | 47.2 | 0 | — | — | — | — | — |
| | | 50% citric acid solution | mL/L | — | — | — | 0 | 0 | 6.5 | — | — | — | — | — |
| | | hydrochloric acid | mL/L | — | — | — | 1 | 0 | 0 | — | — | — | — | — |
| | Treatment | Temp. | ° C. | — | — | — | 45 | 45 | 45 | — | — | — | — | — |
| | | Time | sec. | — | — | — | 10 | 60 | 60 | — | — | — | — | — |
| Plating | Composition | nickel sulfate | g/L | — | 255 | 255 | 255 | 255 | 255 | — | — | — | 255 | — |
| | | nickel chloride | g/L | — | 49 | 49 | 0 | 0 | 0 | — | — | — | 49 | |
| | | sodium citrate | g/L | — | 20 | 20 | 20 | 20 | 20 | — | — | — | 20 | — |

<2. Compression Bonding, and Peeling of Resin Substrates>

(1) Method

Figures 2, 3:
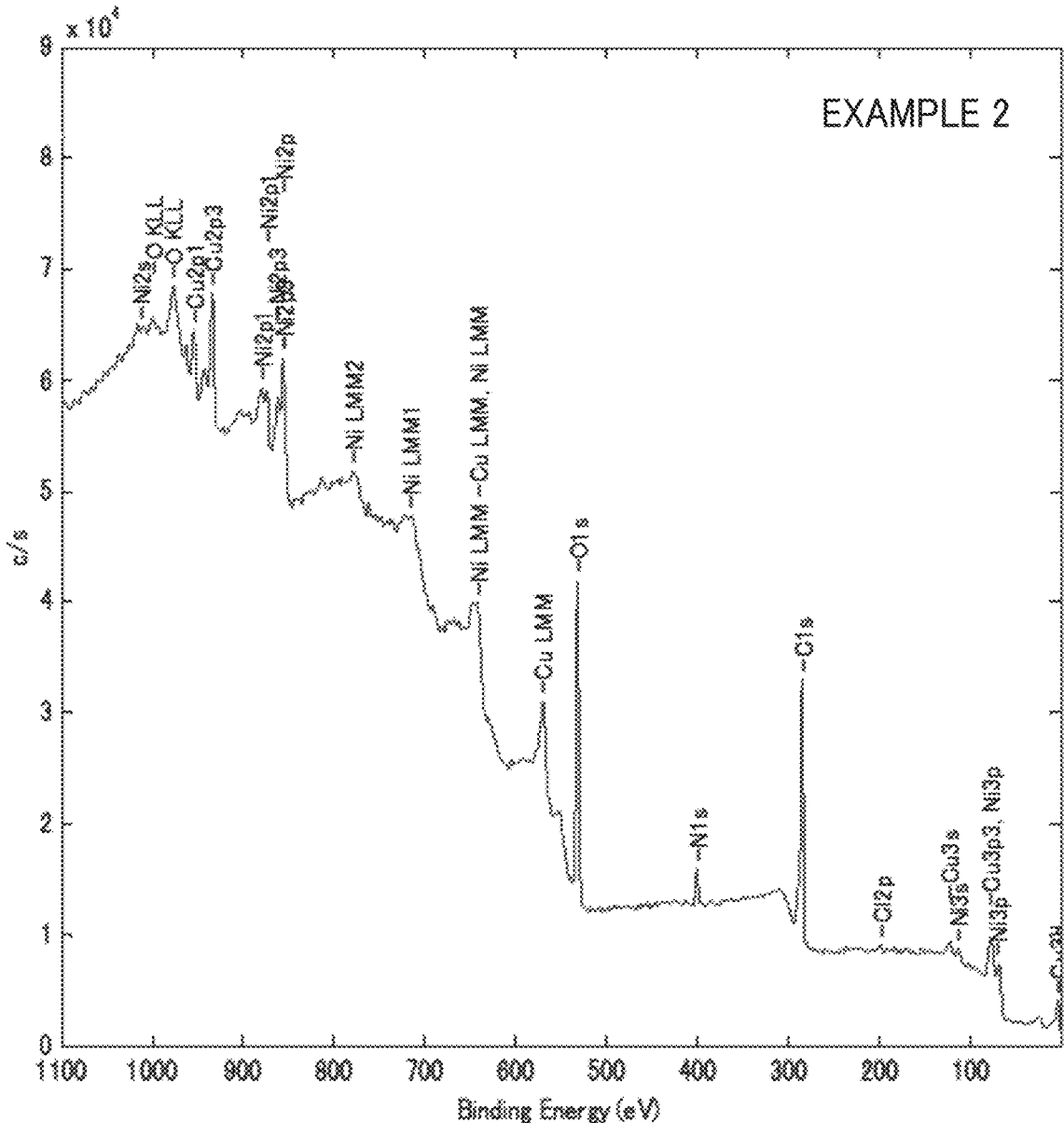
FIG. 2 shows results of visual observation of composite copper foils (FIG. 2-1) (in which white circles indicate that a portion of a copper foil surface was transferred to a resin substrate and cross symbols indicate that no transfer was observed) and representative photographs of the surfaces of the composite copper foils on both sides (FIG. 2-2) in Examples 1-8 and Comparative Examples 2-4 after the copper foils were bonded to the resin substrate by compression and peeled off from there.
Figure 3:
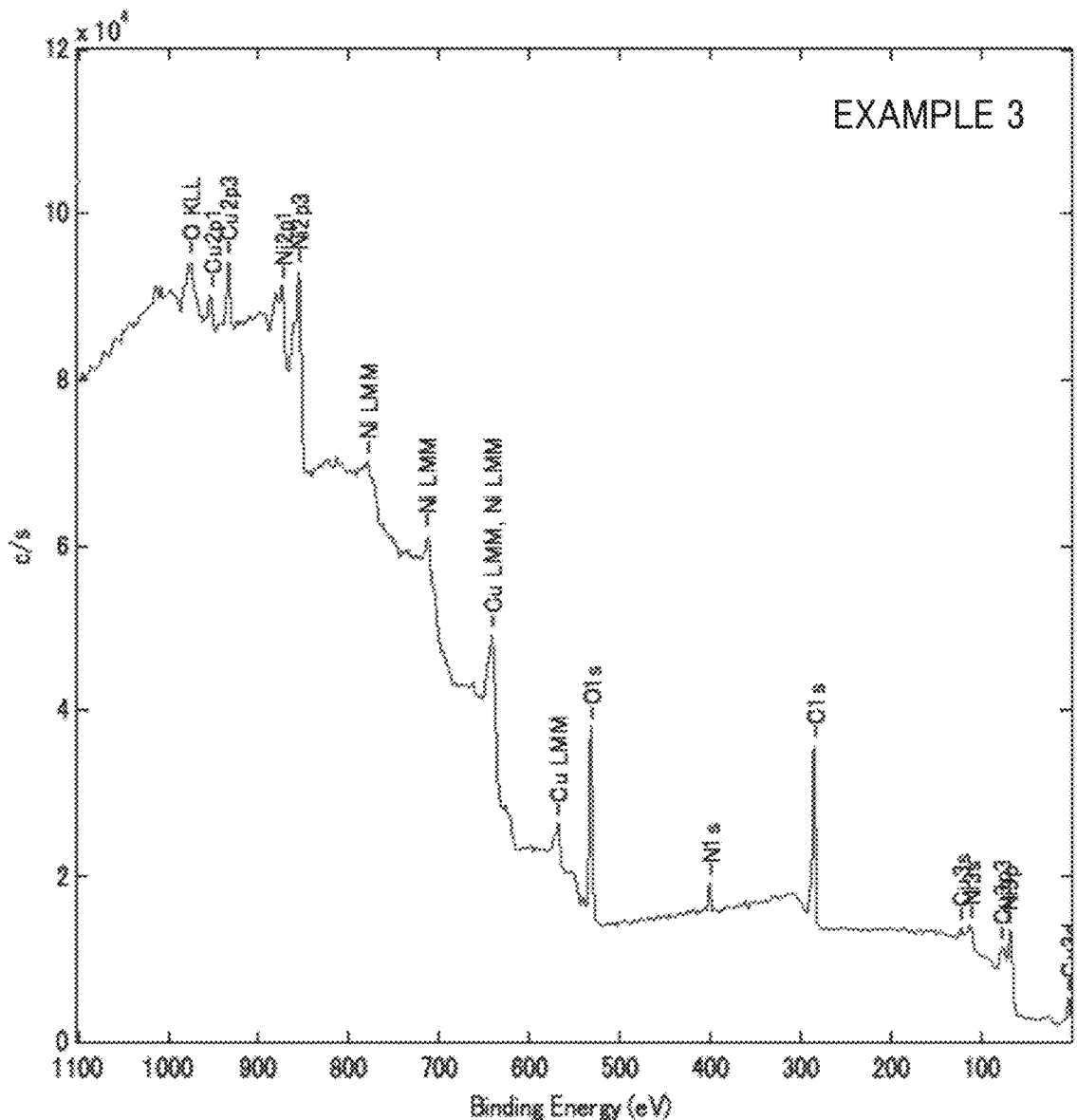
Figures 3, 4:
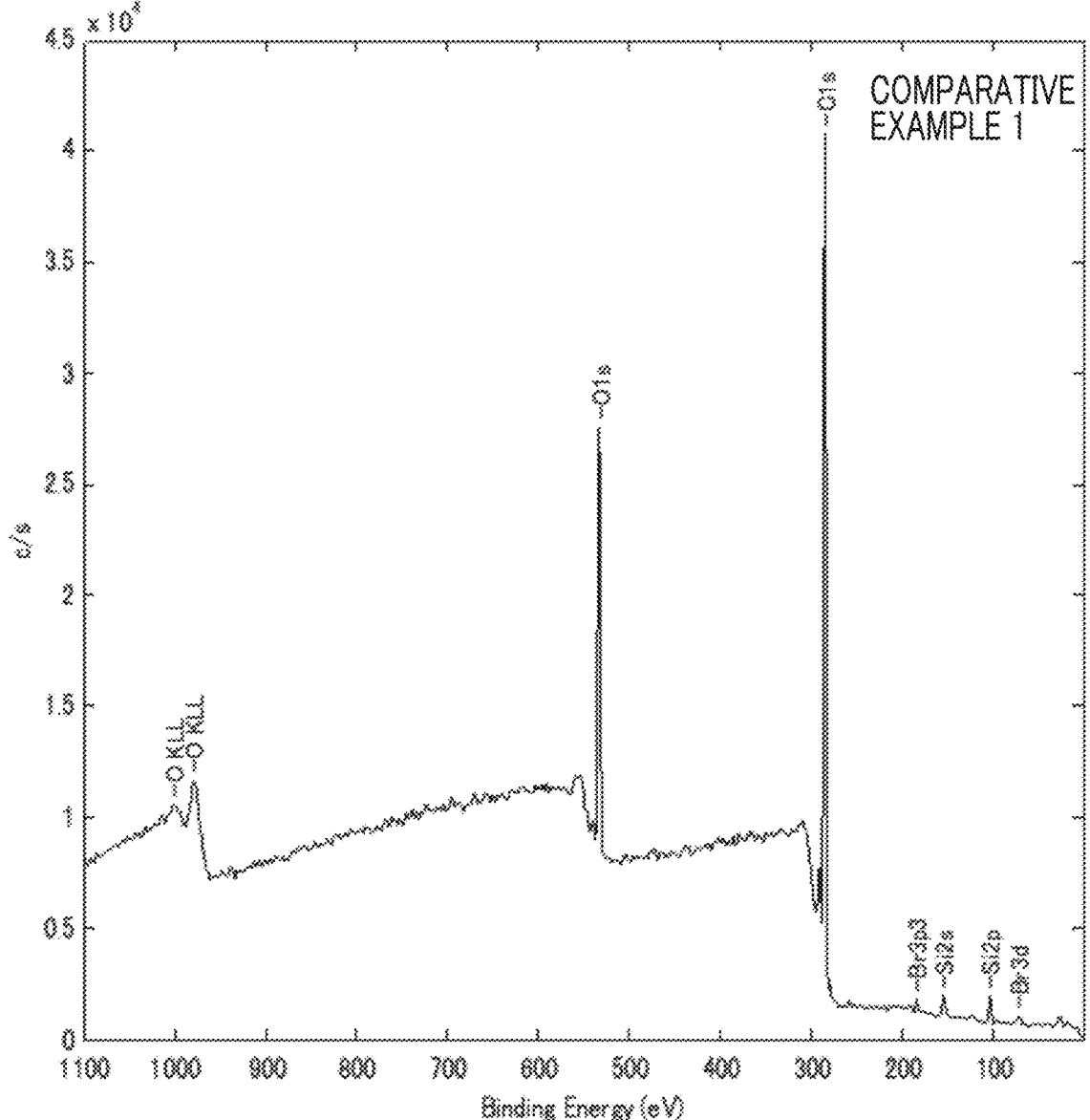
Figures 3, 4, 5:
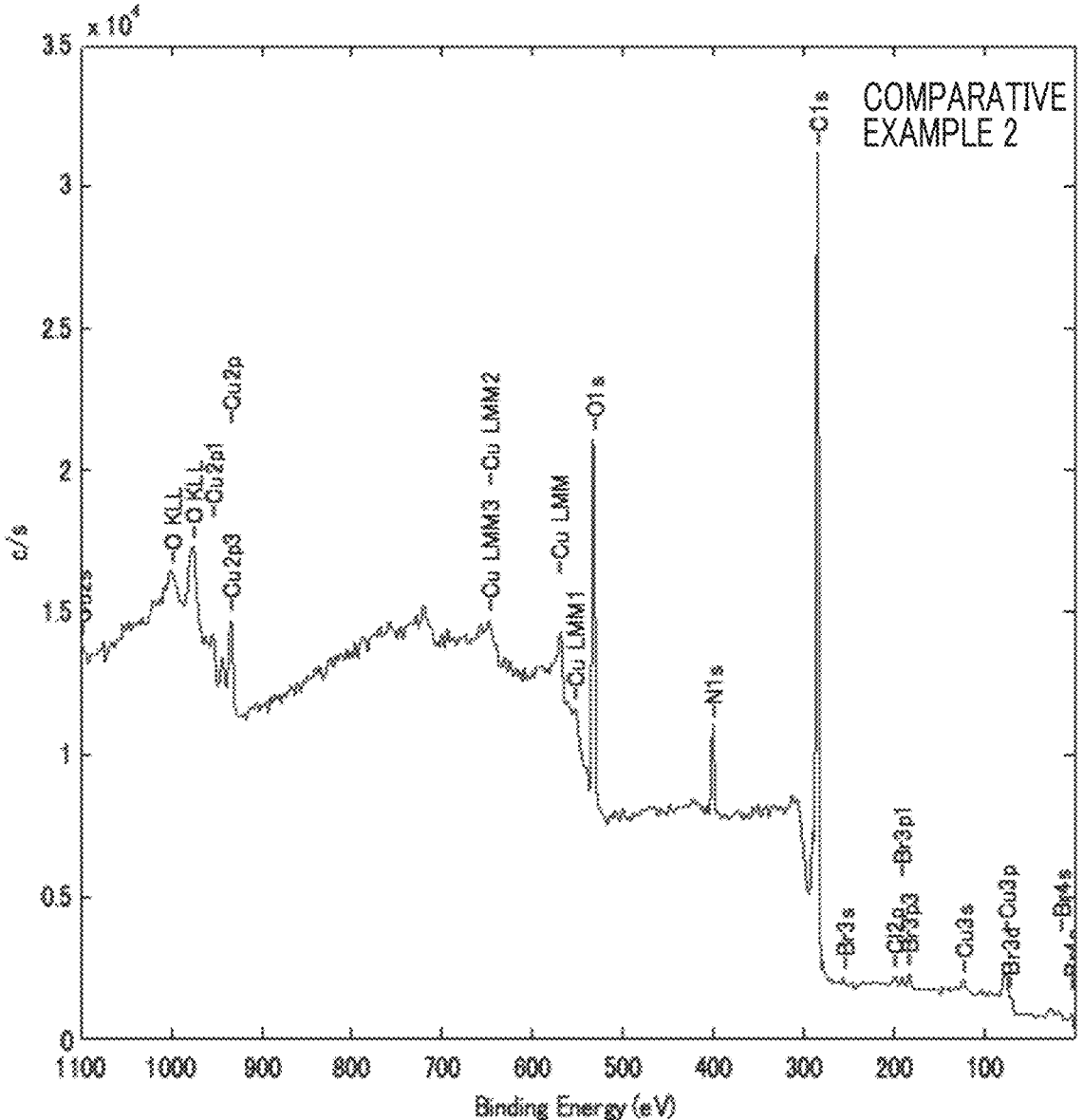
Figures 3, 4, 5, 6:
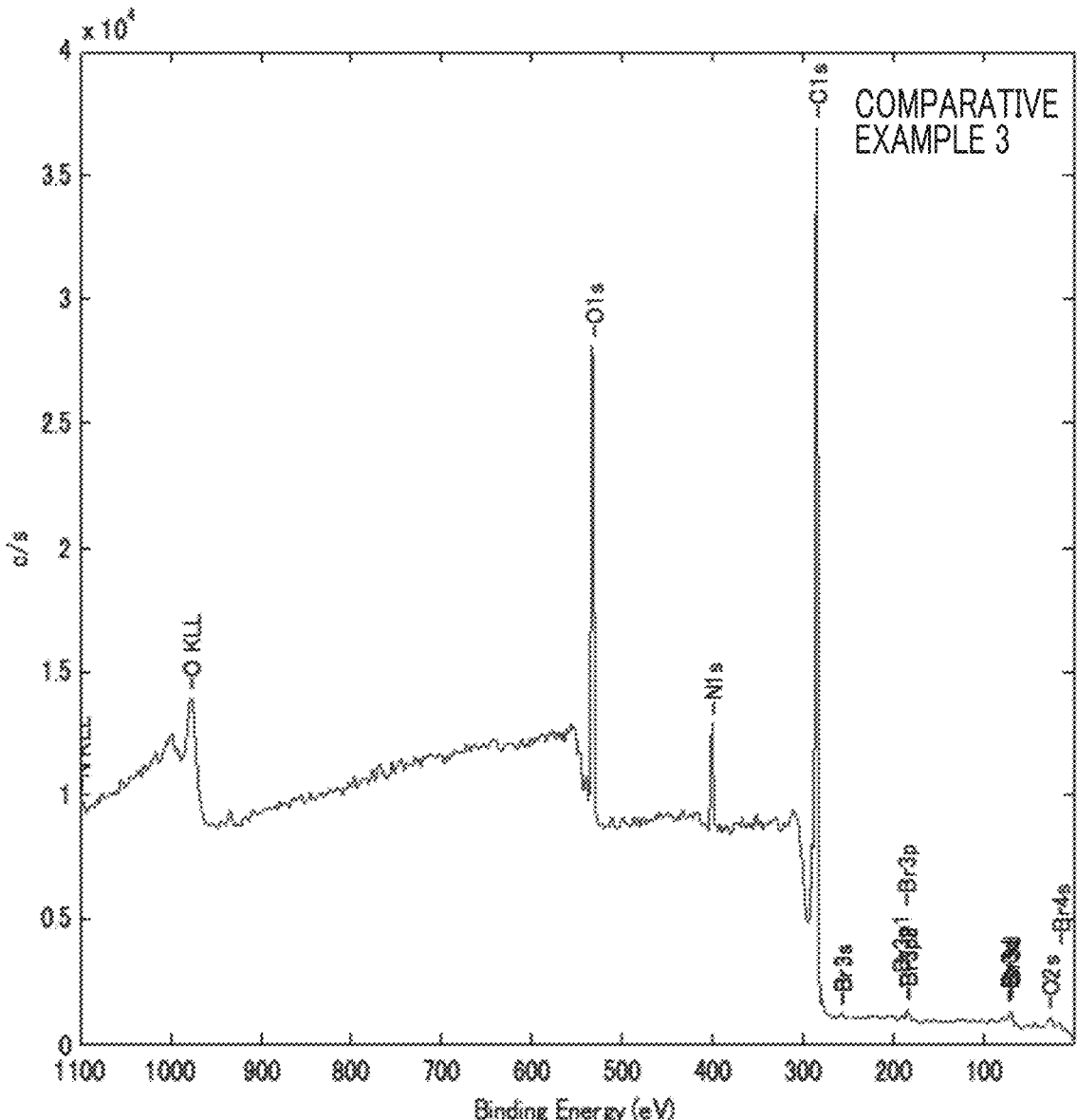
Figures 3, 4, 5, 6, 7:
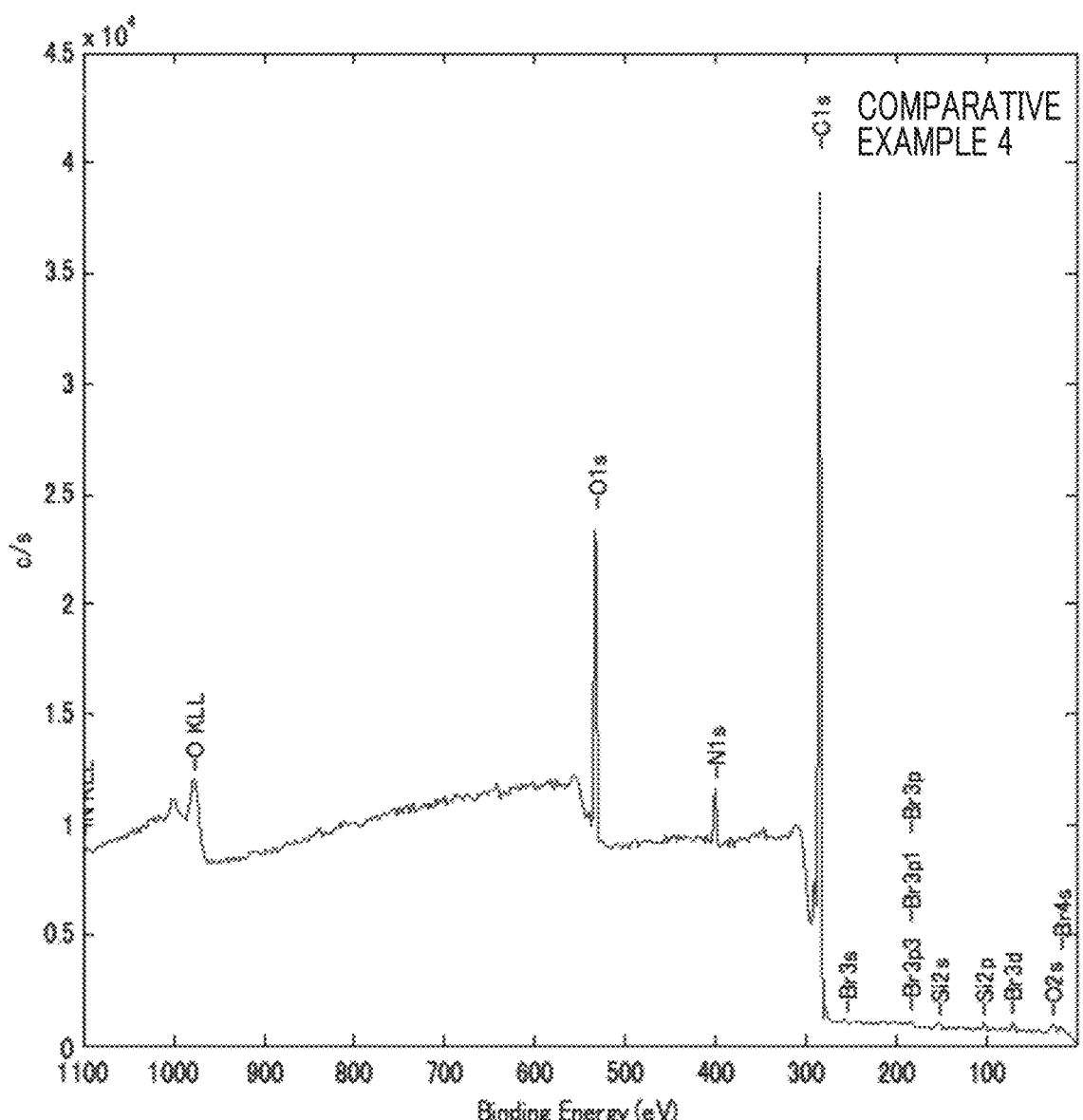
Figures 1, 4:
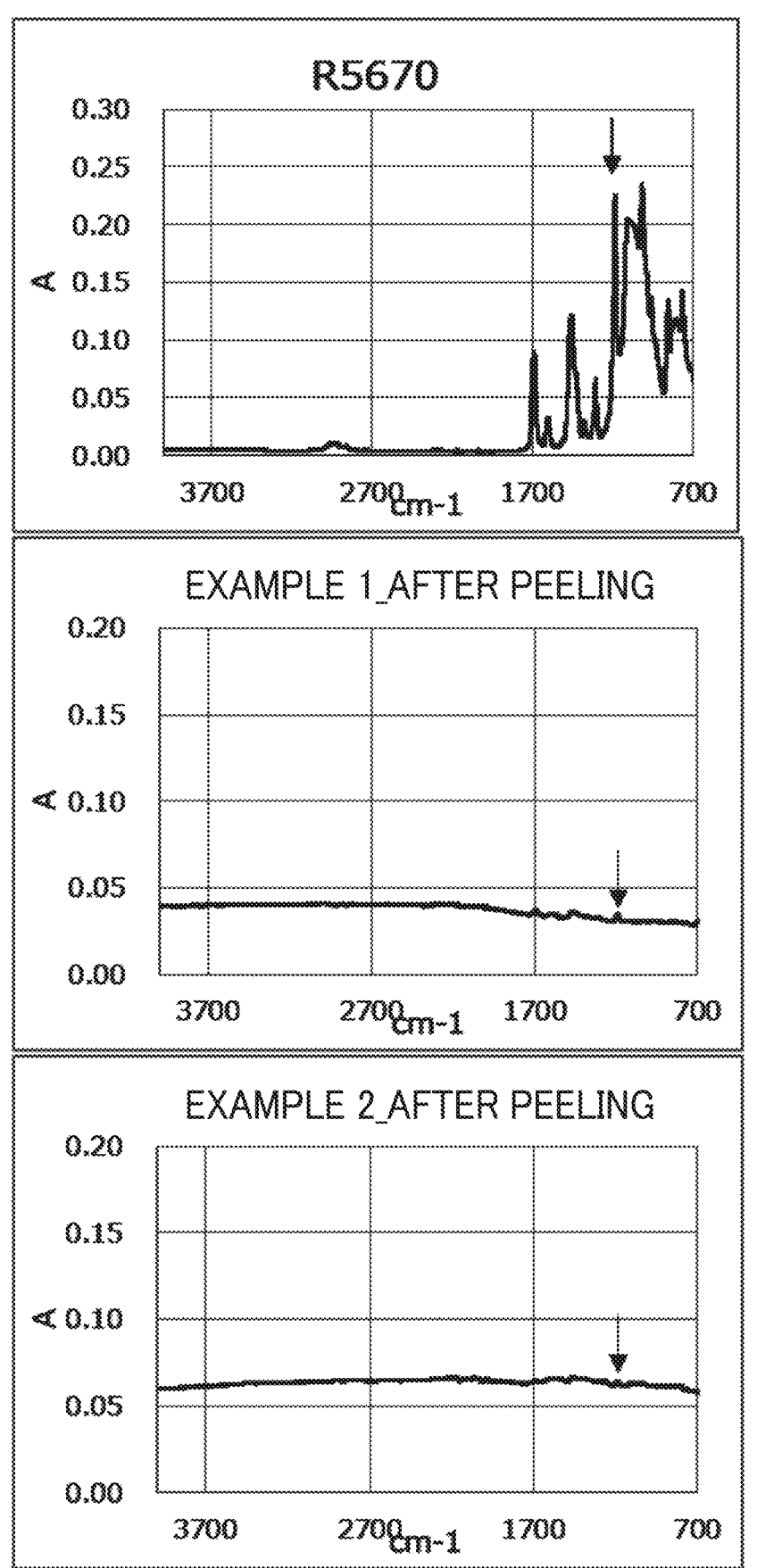
Figures 3, 4:
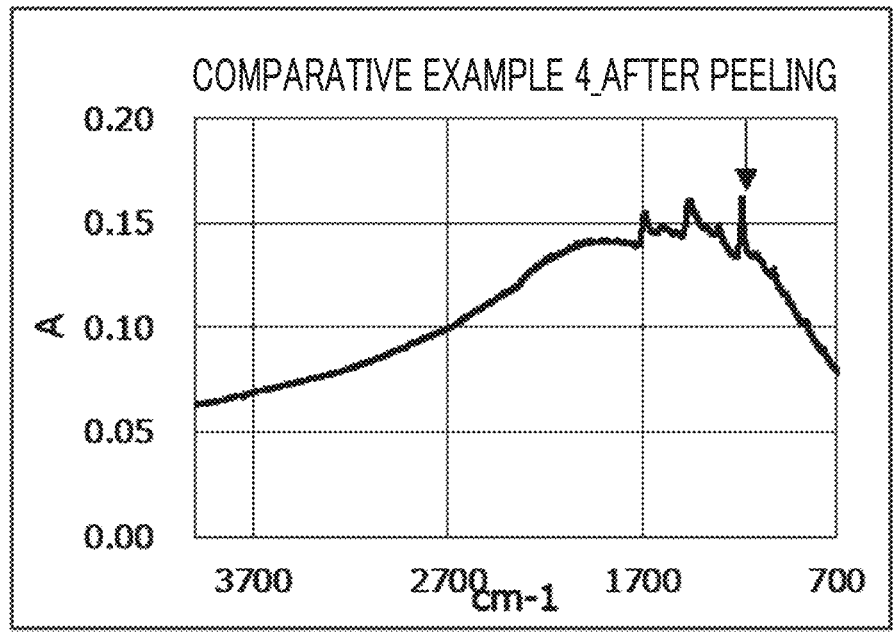
Figures 2, 6:
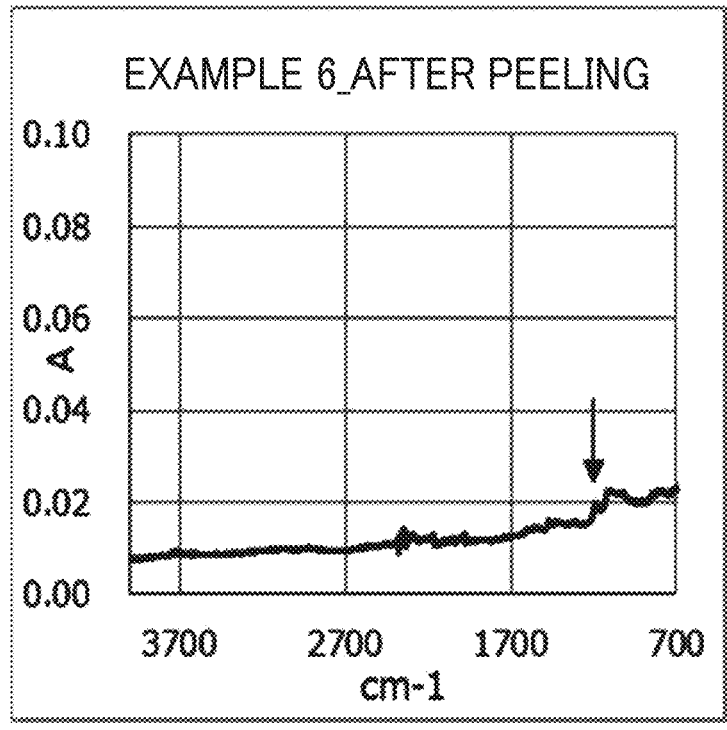
Figure 8:
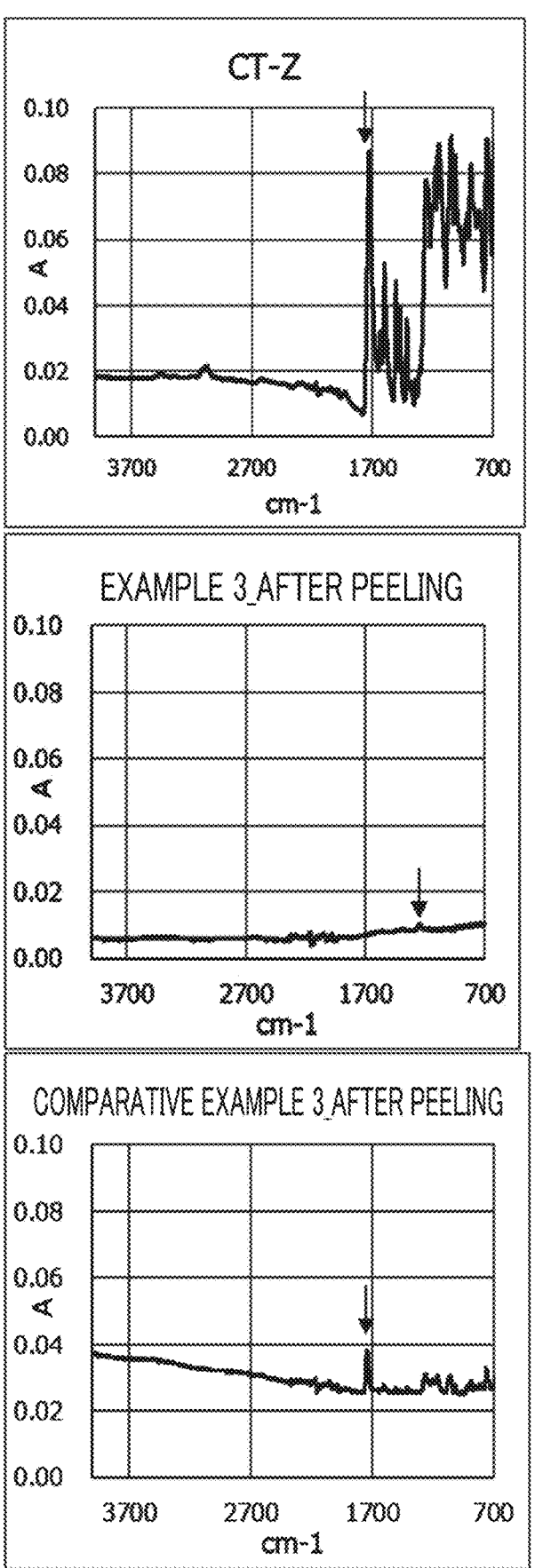
FIG. 8 shows results of ATR FT-IR measurement of surfaces of composite copper foils in the Example 3 and the Comparative Example 3 obtained after the copper foils were bonded to a resin substrate (CT-Z) by thermocompression and peeled off from there.

R5670KJ (manufactured by Panasonic Corp.), R5680J (manufactured by Panasonic Corp.), CT-Z (manufactured by Kuraray Co., Ltd.), NX9255 (manufactured by Park Electrochemical Corp.), and R1551GG (manufactured by Panasonic Corp.) were used as prepregs for the test specimens of heating it while applying a pressure of 0.69 MPa until the temperature reached 260° C., heating it at an increased pressure of 1.5 MPa until the temperature reached 385° C., and holding it at 385° C. for 10 minutes. When the resin substrate was R1551GG (manufactured by Panasonic Corp.), the sample was subjected to thermocompression bonding by heating it at a pressure of 1 MPa and, after the temperature reached 100° C., holding it at this temperature for 10 minutes; subsequently, further heating the sample at a pressure of 3.3 MPa and, after the temperature reached 180° C., holding it at this temperature for 50 minutes. When the resin substrate was CT-Z (Kuraray Co., Ltd.), the sample was subjected to thermocompression bonding by heating it at a pressure of 0 MPa, holding it at 260° C. for 15 minutes, further heating it while applying a pressure of 4 MPa, and holding it at 300° C. for 10 minutes. For these laminated samples, copper components were peeled off from the resin substrate according to the 90° peeling test (Japanese Industrial Standard (JIS) C5016) (FIG. 1). The results of visual observation are given in FIG. 2-1. Photographs of the surfaces of the resin and copper foil sides after the separation are shown in FIG. 2-2 for typical combinations.

was smaller than that of the CIs in the spectrum. This shows that, in the Comparative Examples, copper atoms are hardly transferred to the resin substrate or hardly exist in the surface layer of the resin substrate where XPS can detect them.

In the Example 1, since the composite copper foil was not plated, only the Cu atoms were transferred and detected on the resin substrate side. In the Examples 2 and 3, since the composite copper foil was plated with Ni, both Cu and Ni atoms were transferred and detected on the resin side.

The ratio of C1s was smaller in all Examples compared to the Comparative Examples. It is considered that the percentage of C1s on the surface was relatively smaller in the Examples owing to the transfer of copper oxide or cuprous oxide.

TABLE 2

| | | | Examples | | | | | | | | Comparative Examples | | | |
|---|---|---|---|---|---|---|---|---|---|---|---|---|---|---|
| | | Unit | 1 | 2 | 3 | 4 | 5 | 6 | 7 | 8 | 1 | 2 | 3 | 4 |
| % Comp. | C 1s | atom % | 69.3 | 57.75 | 57.94 | 50.46 | 81.19 | 55.75 | 67.32 | 50.68 | 81.58 | 79.89 | 77.94 | 81.39 |
| | N 1s | atom % | 3.62 | 3.76 | 4.21 | 0 | 1.32 | 0 | 4.76 | 3.9 | 0 | 4.64 | 5.13 | 3.69 |
| | O 1s | atom % | 20.74 | 29.35 | 26.42 | 34.29 | 14.37 | 29.03 | 19.97 | 28.11 | 16.53 | 15.15 | 16.74 | 14.38 |
| | Si 2p | atom % | 0 | 0 | 0 | 0 | 0 | 0 | 0 | 0 | 1.69 | 0 | 0 | 0.42 |
| | Cl 2p | atom % | 0 | 0 | 0 | 0.91 | 0.23 | 2.52 | 1.73 | 2.05 | 0 | 0 | 0 | 0 |
| | Br 3p | atom % | 0 | 0 | 0 | 0 | 0 | 0 | 0 | 0 | 0.2 | 0.32 | 0.19 | 0.13 |
| | Sn 3d5 | atom % | 0 | 0 | 0 | 4.34 | 0 | 0 | 0 | 0 | 0 | 0 | 0 | 0 |
| | Ni 2p | atom % | 0 | 4.33 | 8.41 | 5.68 | 0.67 | 4.18 | 0 | 0 | 0 | 0 | 0 | 0 |
| | Cu 2p3 | atom % | 6.34 | 4.81 | 3.03 | 4.32 | 2.22 | 8.51 | 6.22 | 15.27 | 0 | 0 | 0 | 0 |
| (Total metal elements)/C1s | | | 0.091 | 0.158 | 0.197 | 0.284 | 0.036 | 0.228 | 0.092 | 0.301 | 0 | 0 | 0 | 0 |

From FIG. 2, it can be easily observed that the surface of the copper foil was transferred to the resin side in the Examples, whereas the surface of the copper foil was not transferred to the resin side in the Comparative Examples. To prove this as a material, surface analysis was performed as follows.

<3. Surface Analysis of Resin Substrates after Separation>

Elemental analysis was performed on the surface of the resin substrates after being peeled off. Specifically, the obtained resin substrates were analyzed using Quantera-SXM (manufactured by ULVAC-PHI, Inc.) under the following conditions. As a negative control, an untreated resin substrate (R5670KJ; MEGTRON6) was analyzed (Comparative Example 1).

(1) Survey Spectrum

First, the elements were detected under the following conditions:

X-ray source: Monochromatic Al Kα (1486.6 eV)

X-ray beam diameter: 100 μm (25 wl5 kV)

Pass energy: 280 eV, 1 eV step

Point analysis: #100 μm

Cycle: 8

(2) Results

The results are shown in Table 2 and FIG. 3.

In the Examples, the peak intensity of the Cu2p3 in the spectrum derived from the transferred copper atoms is larger than that of the CIs in the spectrum caused by the resin substrate, whereas in the Comparative Examples the peak of the Cu2p3 in the spectrum was not detected or its intensity <4. Measurement of Ra and Surface Area of Composite Copper Foils Before Thermocompression Bonding and after Peeling>

(1) Method

Surface areas of the composite copper foil specimens of the Examples 1-8 and the Comparative Examples 2-4 were calculated before thermocompression bonding and after peeling using a confocal microscopy OPTELICS H1200 (manufactured by Lasertec Corp.). Measurement conditions used were as follows: using a blue light source, in the confocal mode with a scan area of 100 μm×100 μm and a cutoff of ⅕. The objective and contact lenses were 100× and 14× magnifications, respectively, with a ×1 digital zoom factor and a z-pitch of 10 nm. The data was acquired at three locations. Each surface area was taken as the average of the three locations.

(2) Results

As shown in Table 3, before the thermocompression bonding and after peeling, the values of Ra and the surface area decreased in each Example, whereas they conversely increased in the Comparative Examples. This shows that, in the Examples, all or a part of the protrusions of the composite copper foils were transferred to the resin side, whereas the Comparative Examples are vice versa: a part of the resin was transferred to the composite copper foils.

TABLE 3

|  | Unit | Examples | | | | | |
|  |  | 1 | 2 | 3 | 4 | 5 | 6 |
|---|---|---|---|---|---|---|---|
| Roughness Ra before thermocompression bonding | μm | 0.18 | 0.21 | 0.04 | 0.06 | 0.05 | 0.05 |
| Roughness Ra after peeling | μm | 0.12 | 0.12 | 0.03 | 0.04 | 0.04 | 0.04 |
| Percent change of roughness (after peeling/before compression bonding) | % | 64.48 | 59.42 | 94.29 | 67.80 | 95.56 | 82.61 |
| Surface area S before compression bonding | μm2 | 21453 | 21578 | 10897 | 12185 | 11109 | 11132 |
| Surface area S after peeling | μm2 | 15573 | 16157 | 10642 | 10960 | 11062 | 10855 |
| Percent change of surface area (after peeling/before compression bonding) | % | 72.59 | 74.88 | 97.66 | 89.95 | 99.58 | 97.52 |

|  | Unit | Examples | | Comparative Examples | | |
|  |  | 7 | 8 | 2 | 3 | 4 |
|---|---|---|---|---|---|---|
| Roughness Ra before thermocompression bonding | μm | 0.23 | 0.19 | 0.03 | 0.04 | 0.18 |
| Roughness Ra after peeling | μm | 0.05 | 0.13 | 0.19 | 0.05 | 0.21 |
| Percent change of roughness (after peeling/before compression bonding) | % | 21.46 | 68.95 | 584.85 | 130.56 | 117.71 |
| Surface area S before compression bonding | μm2 | 23636 | 21709 | 10809 | 10915 | 19033 |
| Surface area S after peeling | μm2 | 11421 | 16718 | 17411 | 11599 | 21839 |
| Percent change of surface area (after peeling/before compression bonding) | % | 48.32 | 77.01 | 161.08 | 106.27 | 114.74 |

**<5. Calculation of ΔE*b of Composite Copper Foils Before Thermocompression Bonding and after Peeling>**

(1) Method

Color differences (L*, a*, b*) between the surfaces of the copper foil of each composite copper foil specimen before thermocompression bonding and after peeling were measured, and ΔE*ab was calculated from the obtained values according to the following equation:

$$\Delta E^*ab=[(\Delta L^*)^2+(\Delta a^*)^2+(\Delta b^*)^2]^{1/2}$$

(2) Results

As shown in Table 4, before thermocompression bonding and after peeling, ΔE*ab was 15 or more in the Examples, whereas it was less than 15 in the Comparative Examples. This is because, in the Examples, the metal contained in the copper oxide-containing layer is transferred to the resin substrate, resulting in a larger color change of the copper component: in contrast, in the Comparative Examples, the copper oxide-containing layer remains on the copper component, resulting in a smaller color change of the copper component. That is to say, the more metal in the copper oxide-containing layer is transferred, the larger the difference between them becomes. In fact, in the photographs shown in FIG. 2, the resin side of the Examples is heavily colored after peeling, while the resin side of the Comparative Examples remains almost white.

TABLE 4

|  |  | Examples | | | | | | | | Comparative Examples | | |
|  |  | 1 | 2 | 3 | 4 | 5 | 6 | 7 | 8 | 2 | 3 | 4 |
|---|---|---|---|---|---|---|---|---|---|---|---|---|
| Before compression bonding | L* | 14.03 | 15.39 | 9.24 | 14.24 | 10.54 | 13.78 | 14.49 | 12.70 | 28.05 | 8.90 | 52.79 |
|  | a* | −1.33 | 0.79 | 0.25 | −0.25 | 0.38 | 0.07 | 2.34 | −0.35 | 10.77 | 0.22 | 18.44 |
|  | b* | 3.11 | 0.53 | 1.25 | −2.40 | 0.38 | 0.58 | 7.08 | −0.56 | 22.48 | 1.47 | 16.57 |
| After peeling | L* | 47.18 | 40.41 | 41.06 | 33.88 | 37.02 | 33.18 | 50.76 | 39.31 | 37.35 | 17.12 | 44.87 |
|  | a* | 8.86 | 9.07 | 4.94 | 7.12 | 7.72 | 7.60 | 12.15 | 4.45 | 11.89 | 7.53 | 13.81 |
|  | b* | 15.60 | 12.05 | 9.62 | 4.91 | −1.35 | 0.50 | 11.79 | 9.79 | 16.11 | −3.81 | 12.81 |
| Color change | ΔL | −33.15 | −25.02 | −31.82 | −19.64 | −26.48 | −19.40 | −36.27 | −26.61 | −9.30 | −8.22 | 7.92 |
|  | Δa | −10.19 | −8.28 | −4.69 | −7.37 | −7.34 | −7.53 | −9.81 | −4.80 | −1.12 | −7.31 | 4.63 |
|  | Δb | −12.69 | −11.52 | −8.37 | −7.31 | 1.73 | 0.08 | −4.71 | −10.35 | 6.37 | 5.28 | 3.76 |
|  | ΔE*ab | 36.90 | 28.80 | 33.20 | 22.21 | 27.53 | 20.81 | 37.87 | 28.95 | 11.33 | 12.20 | 9.91 |

23

<6. Analysis of Composite Copper Foil Surfaces after Transfer by Attenuated Total Reflection Fourier Transform Infrared Spectroscopy (ATR FT-IR)>
(1) Method As the resin substrates, R1551GG (epoxy-based), R5670KJ and R5680J (PPE-based), NX9255 (PTFE-based), and CT-Z (LCP-based) were used for thermocompression bonding, and composite copper foil specimens after peeling were analyzed using ATR FT-IR under the following measurement conditions.

Measurement conditions:
Parkin Elmer's Spectrum 100
ATR method:

24

The surfaces of the copper components after the transfer were measured using FT-IR, and a baseline was drawn by connecting the extreme points of both ends of the peak at the maximum peak detection wavelength with a straight line. The difference between the baseline and the maximum height of the peak was used as the signal value (S). The difference between the maximum and minimum values of the peak detected at a wavelength of 3800-3850 cm$^{-1}$ was used as the noise value (N), and the S/N ratio was calculated.

(3) Results

The results are shown in FIGS. 4-8 and Table 5.

TABLE 5

| R1551GG | Ex. 3 | Comp. Ex. 3 |
|---|---|---|
| N noise width | 0.00068 | 0.0006 |
| S signal height | 0.0003 | 0.0069 |
| S/N ratio | 0.4 | 11.5 |

| R5670KJ | Examples | | | | | Comparative Examples | | |
|---|---|---|---|---|---|---|---|---|
| | 1 | 2 | 3 | 7 | 8 | 2 | 3 | 4 |
| N noise width | 0.0007 | 0.0004 | 0.0006 | 0.0004 | 0.0004 | 0.0003 | 0.0007 | 0.0011 |
| S signal height | 0.0049 | 0.0026 | 0.0015 | 0.0002 | 0.0002 | 0.0650 | 0.0076 | 0.0281 |
| S/N ratio | 7 | 6.5 | 2.5 | 0.4 | 0.4 | 216.7 | 10.9 | 25.5 |

| R5680J | Examples | | |
|---|---|---|---|
| | 4 | 5 | 6 |
| N noise width | 0.0005 | 0.0007 | 0.0007 |
| S signal height | 0.0013 | 0.0010 | 0.0069 |
| S/N ratio | 2.6 | 1.4 | 9.8 |

| NX9255 | Ex. 3 | Comp. Ex. 3 |
|---|---|---|
| N noise width | 0.000535 | 0.000535 |
| S signal height | 0.0052 | 0.0576 |
| S/N ratio | 9.7 | 107.7 |

| CT-Z | Ex. 3 | Comp. Ex. 3 |
|---|---|---|
| N noise width | 0.00035 | 0.00035 |
| S signal height | 0.0004 | 0.0125 |
| S/N ratio | 1.1 | 35.7 |

Crystal: germanium
Spectral resolution: 4
Scan rate: 4 scans
Pressure (force gauge): 40±5 [N]
Spectrum: absorbance units
(2) Calculation of S/N Ratio After heating and pressurizing only the resin substrate under the same conditions as those used for thermocompression bonding to the composite copper foil, the resin substrate was subjected to FT-IR measurement. An arbitrary wavelength without resin-derived peaks was selected in the range of 50 cm$^{-1}$. In this example, the wavelength range of 3800-3850 cm$^{-1}$ was selected as the wavelength with no peak derived from the resin. Furthermore, in the wavelength range of 700-4000 cm$^{-1}$, the wavelength at which the maximum peak was detected was identified. The maximum peak was detected around 1200 cm$^{-1}$ when R1551GG was used as the resin substrate; likewise, around 1190 cm$^{-1}$ for R5670KJ and R5680J, around 1232 cm$^{-1}$ for NX9255, and around 1741 cm$^{-1}$ for CT-Z (arrowheads in FIGS. 4-8 represent the detected maximum peak wavelengths).

As shown in Table 5, in the Examples, no peak with S/N ratios of 10 or higher corresponding to resin-derived organic matter was detected on the composite copper foil side. In contrast, in the Comparative Examples, peaks with S/N ratios of 10 or higher corresponding to resin-derived organic matter were detected on the composite copper foil side.

This is because, in the Comparative Examples, the metal on the surface of the composite copper foil was hardly transferred, the cohesive destruction of the resin occurred when the composite copper foil was peeled off from the resin substrate; and the destroyed resin adhered to the surface of the composite copper foil, so the peak corresponding to the organic matter derived from the resin was detected. In the Examples, however, since the metal on the surface of the composite copper foil was transferred to the resin substrate, there was almost no adhesion of the resin to the composite copper foil after it was peeled off from the resin substrate, and no peak with S/N ratios of 10 or higher corresponding to resin-derived organic matter was detected.

In other words, the metal on the surface of the composite copper foil is not transferred and cohesive destruction of the resin occurs because the protrusions formed with the copper oxide-containing layer are stronger than the resin substrate in the Comparative Examples. In contrast, the metal on the surface of the composite copper foil is transferred and the resin hardly adheres because the protrusions formed with the copper oxide-containing layer are weaker than the resin substrate in the Examples.

[2] Analysis of Laminates

First, a composite copper foil in Example was prepared by the following processes (1) to (3) using a shiny side (a glossy side, which is flatter compared with the opposite side) of a copper foil (DR-WS, thickness: 18 μm), manufactured by FURUKAWA ELECTRIC CO., LTD. (Example 9). As Comparative Example, an ultra-thin copper foil on a carrier (MT18FL, thickness of the ultra-thin copper foil: 3 μm) manufactured by MITSUI MINING & SMELTING CO., LTD. was used as it is (Comparative Example 5). Laminates were prepared for these copper foils in a similar manner as described in (4) below and analyzed as described in (5).

(1) Pretreatment

The copper foils were immersed in 10 g/L of potassium carbonate and a solution of 0.06 g/L of potassium hydrogen carbonate at 25° C. for 1 minute.

(2) Oxidation Treatment

The pretreated copper foils were immersed in an oxidizing agent for oxidation treatment.

A solution of 46.3 g/L of sodium chlorite, 12.3 g/L of potassium hydroxide, and 2.1 g/L of KBM-403 (3-glycidoxypropyltrimethoxysilane; manufactured by Shin-Etsu Silicone) was used as an oxidizing agent, and the copper foils were immersed in the solution at 73° C. for 2 minutes.

(3) Electrolytic Plating

After the oxidation treatment, electrolytic plating was performed using an electrolytic nickel-plating solution (nickel sulfate 255 g/L, nickel chloride 49 g/L, and sodium citrate 20 g/L). The copper foil was immersed in an electrolytic nickel-plating solution for 1 minute before electrolytic plating. The electrolytic plating was performed at 50° C. and a current density of 0.5 A/dm$^2$×45 s (=22.5 C/dm$^2$ copper foil area).

(4) Lamination

Next, R5680NJ (manufactured by Panasonic Corp.) was laminated as a prepreg to test specimens, which were subjected to thermocompression bonding while heating them until the temperature reached 110° C. under vacuum at a pressure of 0.5 MPa using a vacuum high-pressure press machine; subsequently, they were subjected to thermocompression bonding while heating them at a pressure of 3.5 MPa for 75 minutes until the temperature reached 195° C. to obtain laminated samples.

Subsequently, a seed layer was formed on each resin substrate by peeling off the composite copper foil by hand to cause the fine protrusions formed on the composite copper foil to transfer onto the resin substrate. Then, electrolytic copper-plating was performed using a commercially available electrolytic copper-plating solution at 30° C. and a current density of 1 A/dm$^2$ for 30 minutes to form an electrolytic copper-plated film of 15 μm thick.

For each laminate thus obtained, a cross section perpendicular to the copper layer was exposed using an ion milling system (E-3500 manufactured by Hitachi High-Technologies Corporation), and the cross section was analyzed as follows.

(5) Elemental Mapping by EDS

Elemental mapping by an energy dispersive X-ray spectroscope (EDS) (Oxford Instruments Plc, product name: X-Max Extreme) was performed on the cross section of each laminate. When performing the analysis, the acceleration voltage of 2 kV and the magnification of 30,000× were used, and SEM images were produced with color-coded elemental distributions based on the detected elemental peak information. The images obtained are given in FIG. 9.

(6) Results

FIG. 9A depicts detection results for the elements C, O, Cu, and Ni. For oxygen atoms (O), oxygen is detected in the seed layer located between the dotted lines on the laminate in the Example. This is considered to be caused by the oxidation treatment of the copper foil during the manufacturing process. In contrast, no oxygen atoms are detected in the seed layer on the laminate in the Comparative Example.

FIG. 9B depicts images obtained by overlaying the detection results for the indicated combinations of the elements. In the images showing O+Cu and C+O in the Example, oxygen atoms are being detected in the seed layer.

FIG. 9C depicts schematic illustrations obtained by overlaying Cu and O.

As can be apparent from the above, the oxygen atoms are detected in the seed layer of the laminate for wiring boards according to the present disclosure.

[3] Circuit Analysis

<Formation of Circuits>

In Examples 10-13, composite copper foils were prepared under the following conditions using a shiny side (a glossy side, which is flatter compared with the opposite side) of a copper foil (DR-WS, thickness: 18 μm), manufactured by FURUKAWA ELECTRIC CO., LTD. In Comparative Example 6, an ultra-thin copper foil on a carrier (MT18FL, thickness of the ultra-thin copper foil: 1.5 μm) manufactured by MITSUI MINING & SMELTING CO., LTD. was used as it is. In Comparative Example 7, an ultra-thin copper foil on a carrier (MT18FL, thickness of the ultra-thin copper foil: 3 μm) manufactured by MITSUI MINING & SMELTING CO., LTD. was used as it is. In Comparative Example 8, an ultra-thin copper foil on a carrier (FUTF-3WAF-2, thickness of the ultra-thin copper foil: 2 μm) manufactured by FUKUDA METAL FOIL & POWDER CO., LTD. was used as it is.

(1) Pretreatment

The copper foils were immersed in a solution of 10 g/L of potassium carbonate and 1 vol. % of KBE-903 (3-aminopropyltriethoxysilane; manufactured by Shin-Etsu Silicone) at 25° C. for 1 minute.

(2) Oxidation Treatment

The pretreated copper foils were immersed in an oxidizing agent for oxidation treatment.

A solution of 60 g/L of sodium chlorite, 20.6 g/L of potassium hydroxide, and 40.2 g/L of potassium carbonate was used as an oxidizing agent, and the copper foils were immersed in the oxidizing agent at 73° C. for 2 minutes in the Examples 10 and 11, and at 73° C. for 10 minutes in the Examples 12 and 13.

(3) Electrolytic Plating

After the oxidation treatment, in the Examples 11 and 13, electrolytic plating was performed using an electrolytic nickel-plating solution (255 g/L of nickel sulfate, 49 g/L of nickel chloride, and 20 g/L of sodium citrate). In the Example 11, the electrolytic plating was performed at 50° C. and a current density of 0.5 A/dm$^2$×116 s (=58 C/dm$^2$ copper foil area). In the Example 13, the electrolytic plating was performed at 50° C. and a current density of 0.5 A/dm$^2$× 172 s (=86 C/dm$^2$ copper foil area).

Next, R5670KJ (manufactured by Panasonic Corp.) was laminated as a prepreg, which was subjected to thermocompression bonding while heating it until the temperature reached 110° C. under vacuum at a pressure of 0.49 MPa using a vacuum high-pressure press machine, and then was subjected to thermocompression bonding while heating it at a pressure of 2.94 MPa for 120 minutes until the temperature reached 210° C. to obtain a laminated substrate.

Subsequently, a seed layer was formed on the resin substrate by peeling off the composite copper foil by hand to cause the fine protrusions formed on the composite copper foil to transfer onto the resin substrate. A commercially available photosensitive dry film was bonded to the formed seed layer, which was exposed through a mask, and developed using 0.8% sodium hydrogen carbonate to form a plating resist.

Then, electrolytic copper-plating was performed using a commercially available electrolytic copper-plating solution at 30° C. and a current density of 1 A/dm² for 30 minutes to form an electrolytic copper-plated film of 15 μm thick.

Furthermore, after Peeling Off and Removing the Plating Resist Using 5% Potassium Hydroxide, the seed layer under the plating resist was dissolved and removed by etching using a mixture of sulfuric acid and hydrogen peroxide to obtain a laminated wiring circuit board (FIG. 11).

<Evaluation of Copper Wiring I: Etching Factors>

Figure 14:
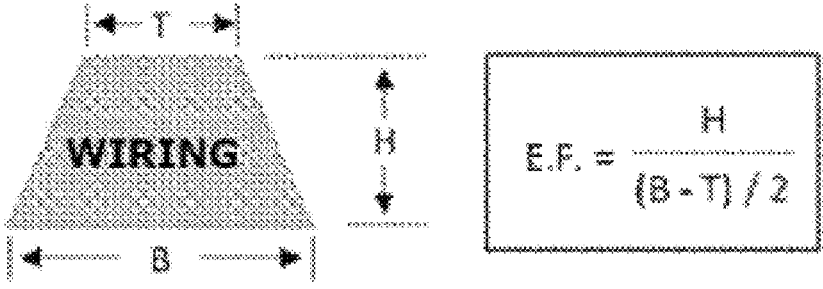
FIG. 14 shows an equation for calculating an etching factor (E.F.).

The shapes of the copper wires were identified using a confocal microscope OPTELICS H1200 (manufactured by Lasertec Corporation), and etching factors were calculated using the equation in FIG. 14.

The results are shown in Table 6 below.

TABLE 6

| | | Examples | | | Comparative Examples | | |
|---|---|---|---|---|---|---|---|
| | | 10 | 11 | 12 | 13 | 6 | 7 | 8 |
| T | μm | 7.28 | 6.76 | 7.93 | 8.06 | 5.20 | 2.47 | 5.37 |
| B | μm | 14.04 | 14.34 | 14.49 | 13.78 | 13.26 | 13.08 | 15.30 |
| H | μm | 14.45 | 14.40 | 14.83 | 13.11 | 14.56 | 13.80 | 14.55 |
| | E.F. | 4.28 | 3.80 | 4.52 | 4.58 | 3.61 | 2.60 | 2.93 |

As shown in Table 6, the fetching factors are 3.80 or larger for the Examples, whereas they are 3.61 or smaller for the Comparative examples.

<Evaluation of Copper Wire Shapes II: Circuit Linearity>

Figure 10:
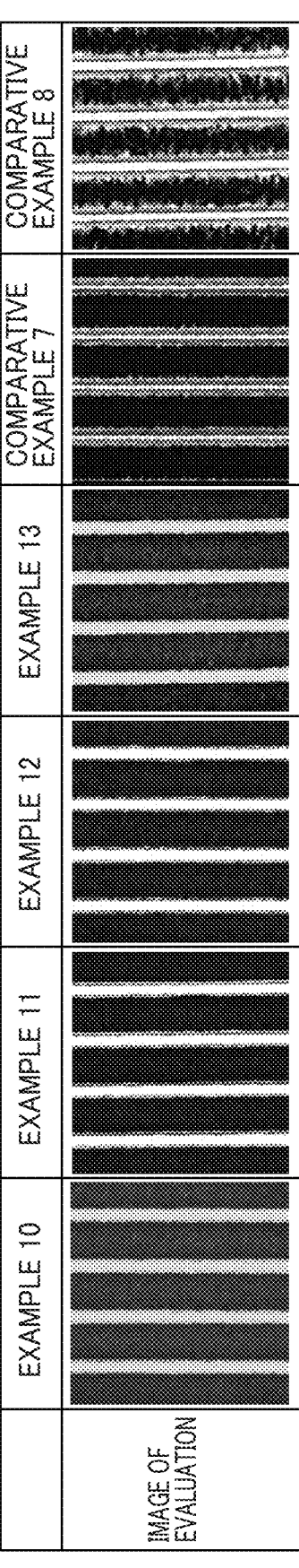
FIG. 10 depicts a layered wiring circuit board manufactured as an example of the present invention.
Figure 15:
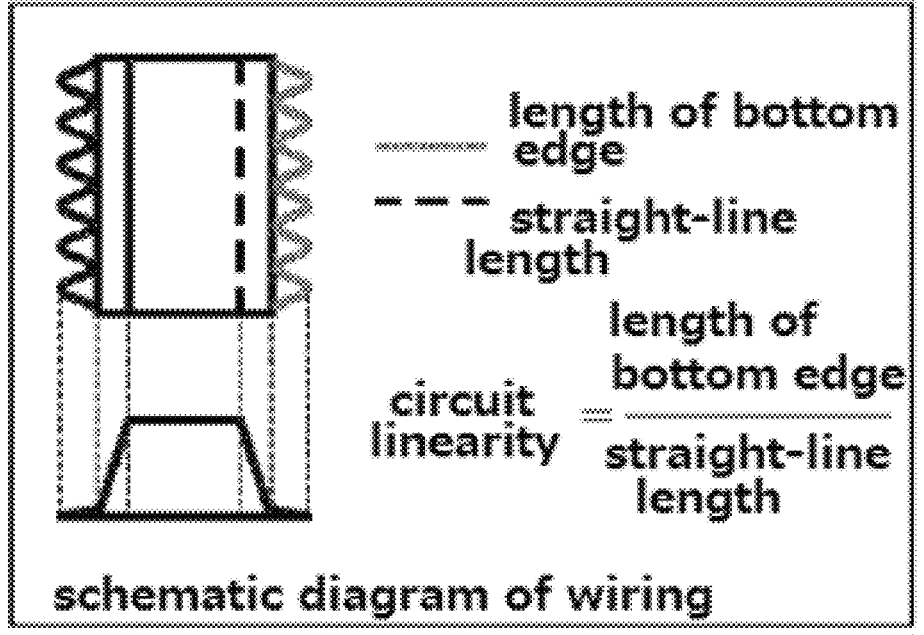
FIG. 15 shows an equation for calculating circuit linearity.

Using the image shown in FIG. 10, circuit linearities (i.e., a value of the ratio of the total length of one side edge of the copper wiring in the longitudinal direction on the surface where the copper wiring contacts the insulating substrate layer to the length of the copper wiring in the longitudinal direction) were calculated using the equation in FIG. 15.

The results are shown in Table 7.

TABLE 7

| | | Examples | | | | Comparative Examples | |
|---|---|---|---|---|---|---|---|
| | | 10 | 11 | 12 | 13 | 7 | 8 |
| Circuit | n1 | 1.266 | 1.395 | 1.179 | 1.235 | 1.581 | 2.852 |
| linearity | n2 | 1.330 | 1.292 | 1.187 | 1.366 | 1.837 | 2.471 |
| | n3 | 1.239 | 1.310 | 1.158 | 1.293 | 1.689 | 3.185 |
| | n4 | 1.270 | 1.421 | 1.250 | 1.295 | 1.877 | 2.936 |
| | n5 | 1.263 | 1.298 | 1.153 | 1.279 | 1.698 | 3.019 |
| | n6 | 1.231 | 1.339 | 1.122 | 1.217 | 1.662 | 3.155 |
| | n7 | 1.340 | 1.503 | 1.175 | 1.311 | 1.734 | 3.415 |
| | n8 | 1.259 | 1.323 | 1.131 | 1.234 | 1.603 | 3.188 |
| | Ave. | 1.275 | 1.360 | 1.169 | 1.279 | 1.710 | 3.028 |

As shown in Table 7, the circuit linearities are 1.7 or less in the Examples, whereas they are greater than 1.7 in the Comparative Examples.

[4] Analysis of Crystal Grains in Seed Layers
(1) Observation of Seed Layers

SEM images of the laminates of the Example 9 and the Comparative Example 5 are shown in FIG. 11. In each image, crystal grains were observed in the seed layer and copper wiring based on the contrast between brightness and darkness reflecting differences in crystal orientation.

In the Example, no contrast between brightness and darkness reflecting differences in crystal orientation could be observed in the seed layer area, and no crystal grain could be detected. The maximum width of the smallest crystal grain present in the copper wiring was determined to be 122 nm, and crystal grains were present in at least 5% relative to the total.

In the Comparative Example, the maximum width of the smallest crystal grain present in the seed layer area was determined to be 118 nm using an 30,000× image, and crystal grains were present in at least 1% relative to the total. In addition, the maximum width of the smallest crystal grain present in the copper wiring was determined to be 124 nm using an 10,000× image, and crystal grains were present in at least 5% relative to the total.

(2) EBSD Analysis

The copper foils used in the Example 9 and the Comparative Example 5 were subjected to pretreatment, oxidation, and electrolytic plating in the same manner, and then laminated as follows to produce laminates of Example 14 and Comparative Example 9. First, R5680NJ (manufactured by Panasonic Corp.) was laminated as a prepreg to the copper foils after being subjected to the electrolytic plating, which were subjected to thermocompression bonding while heating them until the temperature reached 110° C. under vacuum at a pressure of 0.5 MPa using a vacuum high-pressure press machine; subsequently, they were subjected to thermocompression bonding while heating them at a pressure of 3.5 MPa for 75 minutes until the temperature reached 195° C. to obtain laminated samples. Subsequently, a seed layer was formed on each resin substrate by peeling off the composite copper foil by hand to cause the fine protrusions formed on the composite copper foil to transfer onto the resin substrate. Then, electroless copper-plating was performed using a commercially available electroless copper-plating solution at 60° C. for 60 minutes to form an electroless copper-plated film of 2 μm thick. Furthermore, electrolytic copper-plating was performed using a commercially available electrolytic copper-plating solution at 30° C. and a current density of 1 A/dm2 for 30 minutes to form an electrolytic copper-plated film of 15 μm thick.

EBSD analysis was performed on the laminates thus prepared in the Example 14 and the Comparative Example 9. A thermal field-emission scanning electron microscope (TFE-SEM) JSM-6500F (manufactured by JEOL Ltd.) was used as an instrument, a DigiView IV slow scan CCD camera (manufactured by TSL Solutions) was used as a detector, and OIM Data Collection ver.7.x and OIM Analysis ver. 7.x were used as EBSD data collection software and EBSD data analysis software, respectively. The analysis conditions are as follows.

Acceleration voltage: 15 kV

Beam current: 15 nA

Sample tilt: 70 degrees

Figure 12:
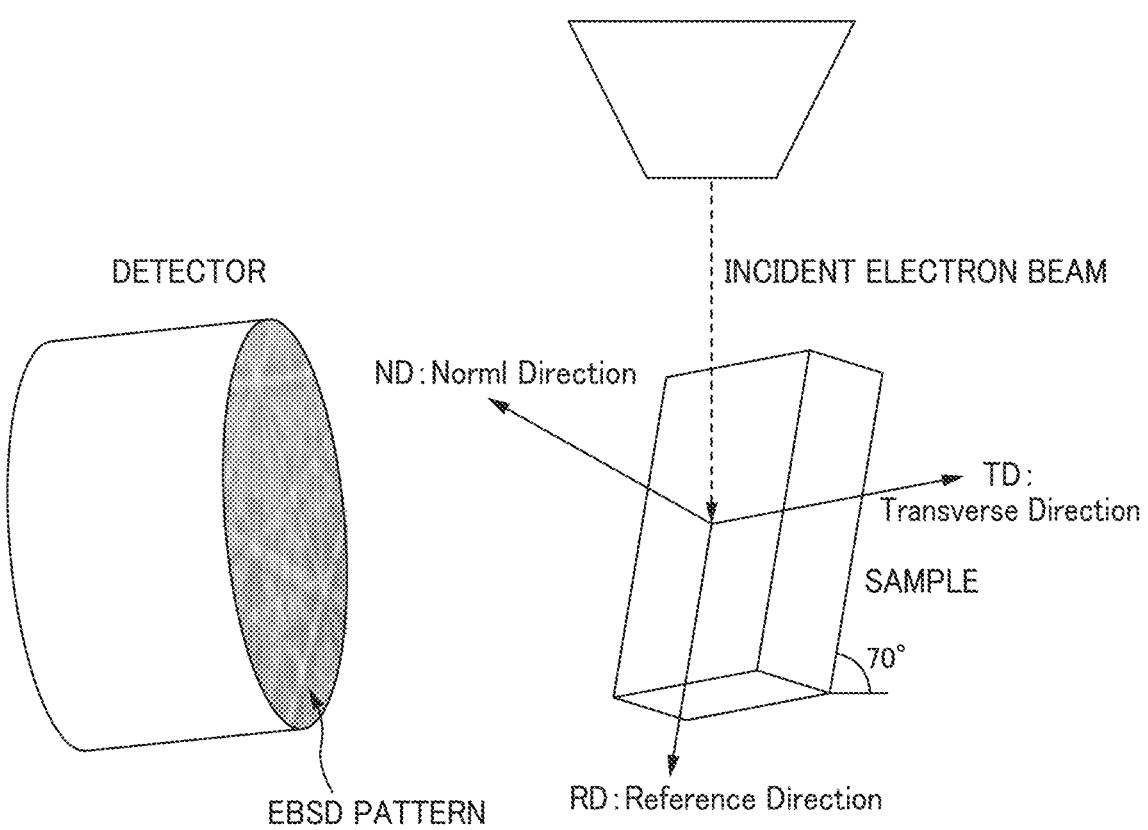
FIG. 12 illustrates a positional relationship between a detector for reflection EBSD and a sample based on a measurement coordinate system, in one example of the present invention.
Figure 13:
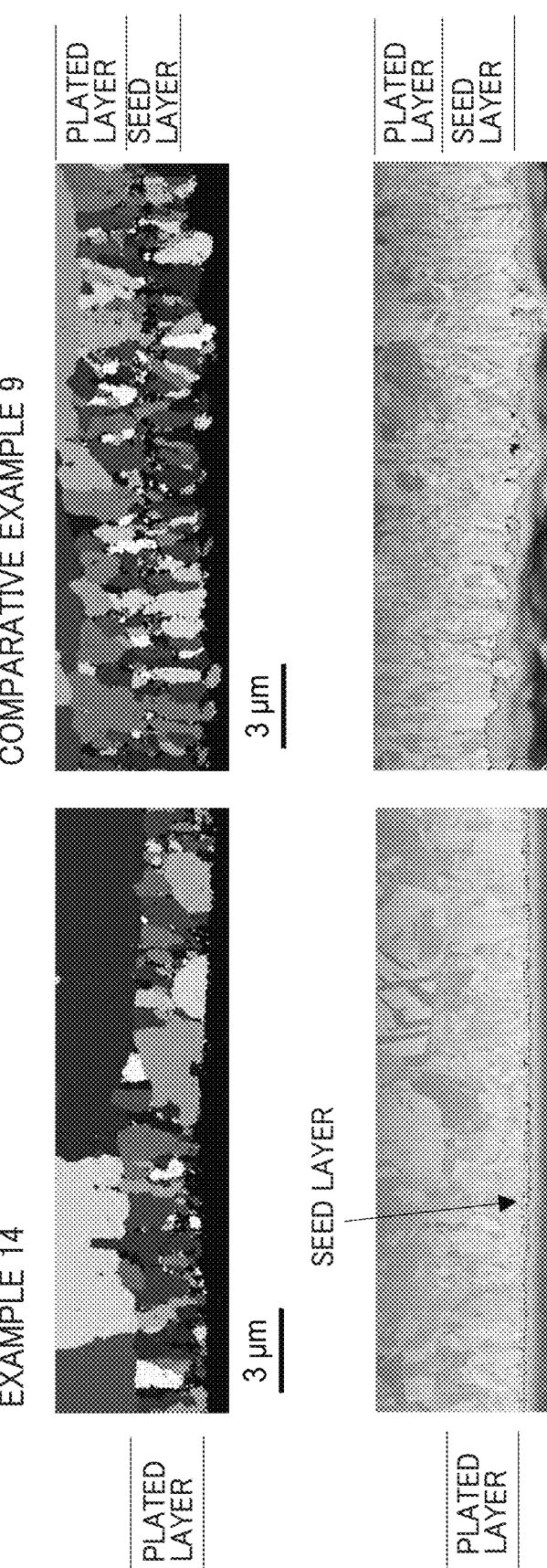
FIG. 13 shows crystal grain maps for an area near the seed layer obtained by EBSD analyses (top) and scanning electron microscope images (×104) taken at the same position (bottom) in one example of the present invention.

Measurement magnification, area, and interval: 3,000×, 20-25 μm×100 μm, and 100 nm/step; and 8,000×, 6 μm×21 μm, and 30 nm/step After the cross sections were processed by mechanical polishing and Ar ion milling under the above conditions, each laminate was fixed to a sample stand and subjected to EBSD analysis (detection limit: 50 nm). FIG. 12 illustrates a positional relationship between the detector for reflection EBSD and a sample based on a measurement coordinate system, and FIG. 13 shows crystal grain maps for an area near the seed layer obtained by EBSD analyses and scanning electron microscope images ($\times 10^4$) taken at the same position. In this analysis, boundaries of twinned crystals were treated as grain boundaries, with an orientation difference between the crystals of 60°±5° and an orientation difference of the twin plane of up to ±1° being allowed.

Using EBSD data analysis software, the size and percentage of crystals were analyzed. In the Comparative Example 9, the percentage of crystals with a maximum grain width of 100 nm or larger was 100%, the percentage of crystals with a maximum grain width of 300 nm or larger was 97%, and the percentage of crystals with a maximum grain width of 500 nm or larger was 91%, whereas in the Example 14, no crystal grain with a maximum width of 50 nm or larger was detected.

INDUSTRIAL APPLICABILITY

The present invention makes it possible to provide novel laminates for circuit boards.

The invention claimed is:

1. A laminate for wiring boards comprising an insulating substrate layer and copper wiring, the laminate having a circuit linearity of 1.0 or more and 1.7 or less,
    wherein a seed layer is present at a boundary between the insulating substrate layer and the copper wiring, and
    wherein the seed layer comprises copper atoms, and
    wherein oxygen is detected in the seed layer in elemental mapping using an energy-dispersive X-ray spectroscope (EDS).

2. The laminate for wiring boards according to claim 1, wherein the seed layer has a thickness of 1.5 μm or smaller.

3. The laminate for wiring boards according to claim 1, wherein the insulating substrate layer has relative permittivity of 5.0 or less.

4. A laminate for wiring boards comprising an insulating substrate layer and copper wiring, the laminate having a circuit linearity of 1.0 or more and 1.7 or less,
    wherein a seed layer is present at a boundary between the insulating substrate layer and the copper wiring, wherein the seed layer comprises copper atoms, and
    wherein crystal grains of copper with a maximum width of 100 nm or larger account for 1% or less relative to the total volume in the seed layer.

5. A laminate for wiring boards comprising an insulating substrate layer and copper wiring, the laminate having a circuit linearity of 1.0 or more and 1.7 or less,
    wherein a seed layer is present at a boundary between the insulating substrate layer and the copper wiring,
    wherein the seed layer comprises copper atoms, and
    wherein a percentage of crystal grains with a maximum width of 500 nm or larger is at least 0% and less than 50% when a size distribution of the crystal grains is measured using electron backscatter diffraction (EBSD) in the seed layer.

6. The laminate for wiring boards according to claim 5, wherein a percentage of crystal grains with a maximum width of 50 nm or larger is at least 0% and less than 50% when a size distribution of the crystal grains is measured using electron backscatter diffraction (EBSD) in the seed layer.

7. A laminate for wiring boards comprising an insulating substrate layer and copper wiring, the laminate having a circuit linearity of 1.0 or more and 1.7 or less,
    wherein a seed layer is present at a boundary between the insulating substrate layer and the copper wiring,
    wherein the seed layer comprises copper atoms, and
    wherein crystal grains with a maximum width of 500 nm or larger is are not detected when a size distribution of the crystal grains is measured using electron backscatter diffraction (EBSD) in the seed layer.

8. The laminate for wiring boards according to claim 7, wherein crystal grains with a maximum width of 50 nm or larger are not detected when a size distribution of the crystal grains is measured using electron backscatter diffraction (EBSD) in the seed layer.

9. A laminate for wiring boards comprising an insulating substrate layer and copper wiring, the laminate having a circuit linearity of 1.0 or more and 1.7 or less,
    wherein a seed layer is present at a boundary between the insulating substrate layer and the copper wiring, and
    wherein a percentage of crystal grains with a maximum width of 500 nm or larger is at least 0% and less than 50% when a size distribution of the crystal grains is measured using electron backscatter diffraction (EBSD) in the seed layer.

* * * * *